US012806310B2

(12) United States Patent
Kyriakides et al.

(10) Patent No.: US 12,806,310 B2
(45) **Date of Patent: *Nov. 24, 2026**

(54) COMPOSITIONS AND METHODS FOR GRAFTS MODIFIED WITH A NON-THROMBOGENIC AND PRO-MIGRATORY CELL-DERIVED EXTRACELLULAR MATRIX

(71) Applicant: YALE UNIVERSITY, New Haven, CT (US)

(72) Inventors: Themis Kyriakides, Branford, CT (US); Nina Kristofik, Wallingford, CT (US)

(73) Assignee: Yale University, New Haven, CT (US)

( * ) Notice: Subject to any disclaimer, the term of this patent is extended or adjusted under 35 U.S.C. 154(b) by 431 days.

This patent is subject to a terminal disclaimer.

(21) Appl. No.: 17/524,038

(22) Filed: Nov. 11, 2021

(65) Prior Publication Data

US 2022/0152273 A1 May 19, 2022

Related U.S. Application Data

(62) Division of application No. 16/095,815, filed as application No. PCT/US2017/029247 on Apr. 25, 2017, now Pat. No. 11,191,872.

(60) Provisional application No. 62/328,222, filed on Apr. 27, 2016.

(51) Int. Cl.

| | |
|---|---|
| ***A61L 27/28*** | (2006.01) |
| ***A61L 27/34*** | (2006.01) |
| ***A61L 27/36*** | (2006.01) |
| ***A61L 27/54*** | (2006.01) |
| ***A61L 29/08*** | (2006.01) |
| ***A61L 31/10*** | (2006.01) |
| ***A61L 33/12*** | (2006.01) |
| ***A61L 33/18*** | (2006.01) |

(52) U.S. Cl.

CPC ............... *A61L 27/28* (2013.01); *A61L 27/34* (2013.01); *A61L 27/3633* (2013.01); *A61L 27/54* (2013.01); *A61L 29/085* (2013.01); *A61L 31/10* (2013.01); *A61L 33/128* (2013.01); *A61L 33/18* (2013.01); *A61L 2300/42* (2013.01); *A61L 2300/606* (2013.01); *A61L 2430/20* (2013.01)

(58) Field of Classification Search

None

See application file for complete search history.

(56) References Cited

U.S. PATENT DOCUMENTS

| | | | |
|---|---|---|---|
| 5,643,712 | A | 7/1997 | Brasile |
| 2009/0318334 | A1 | 12/2009 | Varadhachary et al. |
| 2014/0220548 | A1 | 8/2014 | Brasile |

FOREIGN PATENT DOCUMENTS

| | | | |
|---|---|---|---|
| CN | 101366976 | A | 2/2009 |
| WO | 9421116 | A1 | 9/1994 |
| WO | 0209735 | A2 | 2/2002 |
| WO | 2014189835 | A2 | 11/2014 |

OTHER PUBLICATIONS

Funamoto et al., Biomaterials, vol. 31, Issue 13, May 2010, pp. 3590-3595 (Year: 2010).*

Extended European Search Report for European Patent Application No. 17790213.7 issued Nov. 19, 2019.

International Search Report and Written Opinion for PCT International Application No. PCT/US2017/029247 issued Jul. 27, 2017.

Attwood , et al., "Measurement of the Interaction Between Recombinant I-domain From Integrin Alpha 2 Beta 1 and a Triple Helical Collagen Peptide With the GFOGER Binding Motif Using Molecular Force Spectroscopy", Int J Mol Sci. 14(2), Jan. 2013, 2832-2845.

Calabro , et al., "Thrombospondin-2 and extracellular matrix assembly", Biochim Biophys Acta. 1840(8), Aug. 2014, 2396-2402.

Kee , et al., "Platelet Mechanosensing of Collagen Matrices", PLoS One. 10(4), Apr. 2015, e0126624.

Krady , et al., "Thrombospondin-2 Modulates Extracellular Matrix Remodeling During Physiological Angiogenesis", Am J Pathol. 173(3), Sep. 2008, 879-891.

Kyriakides , et al., "Megakaryocytes Require thrombospondin-2 for Normal Platelet Formation and Function", Blood. 101(10), May 2003, 3915-3923.

Kyriakides , et al., "Mice that lack thrombospondin 2 display connective tissue abnormalities that are associated with disordered collagen fibrillogenesis, an increased vascular density, and a bleeding diathesis", J Cell Biol. 140(2), Jan. 1998, 419-430.

Morris , et al., "Matricellular Proteins and Biomaterials", Matrix Biol. 37, Jul. 2014, 183-191.

Qiu , et al., "Platelet Mechanosensing of Substrate Stiffness During Clot Formation Mediates Adhesion, Spreading, and Activation", Proc Natl Acad Sci U S A. 111(40), Oct. 2014, 14430-14435.

Roh , et al., "Small-diameter biodegradable scaffolds for functional vascular tissue engineering in the mouse model", Biomaterials. 29(10), Apr. 2008, 1454-1463.

Soucy , et al., "Microelastic Properties of Lung Cell-Derived Extracellular Matrix", Acta Biomater. 7(1), Jan. 2011, 96-105.

(Continued)

*Primary Examiner* — Evelyn Y Pyla

(74) *Attorney, Agent, or Firm* — Saul Ewing LLP; Kathryn Doyle; Peter Brunovskis

(57) ABSTRACT

The present invention relates to novel compositions and methods for reducing or eliminating the thrombogenicity of a graft by modifying the graft with a cell-derived extracellular matrix lacking thrombospondin-2 (TSP2-null ECM) to render it non-thrombogenic when transplanted to a subject in need thereof. The invention also provides a method for improving the biocompatibility of a medical device or an implant by modifying the medical device or implant with a cell-derived TSP2-null ECM, whereby the medical device or implant is rendered non-thrombogenic and pro-migratory.

8 Claims, 25 Drawing Sheets

Specification includes a Sequence Listing.

(56) References Cited

OTHER PUBLICATIONS

Szántó , et al., “New Insights Into Von Willebrand Disease and Platelet Function”, Semin Thromb Hemost. 38(1), Feb. 2012, 55-63 (Abstract Only).
Yoo , et al., “A Novel in Vitro Model of Lymphatic Metastasis From Colorectal Cancer”, J Surg Res. 143(1), Nov. 2007, 94-98 (Abstract Only).
Zhu , et al., “Determination of Mechanical Properties of Soft Tissue Scaffolds by Atomic Force Microscopy Nanoindentation”, J Biomech. 44(13), Sep. 2011, 2356-2361 (Abstract Only).
Merriam-Webster, definition of Intact, retrieved from the internet (Apr. 27, 2021): https://www.merriam-webster.com/dictionary/intact ( Year: 2021).

* cited by examiner

F

COMPOSITIONS AND METHODS FOR GRAFTS MODIFIED WITH A NON-THROMBOGENIC AND PRO-MIGRATORY CELL-DERIVED EXTRACELLULAR MATRIX

CROSS-REFERENCE TO RELATED APPLICATION

This application is a divisional of U.S. application Ser. No. 16/095,815, filed Oct. 23, 2018, now U.S. Pat. No. 11,191,872, which is a 35 U.S.C. § 371 national phase application from, and claims priority to, International Application No. PCT/US2017/029247, filed Apr. 25, 2017, and published under PCT Article 21(2) in English, which claims priority to U.S. Provisional Application Ser. No. 62/328,222, filed Apr. 27, 2016, the content of each of which is incorporated by reference herein in its entirety.

STATEMENT REGARDING FEDERALLY SPONSORED RESEARCH OR DEVELOPMENT

This invention was made with government support under Grants Nos. HL107205 and HL083895 awarded by the National Institutes of Health. The government has certain rights in the invention.

BACKGROUND OF THE INVENTION

Cardiovascular disease is the leading cause of mortality in the USA and coronary and peripheral vascular bypass graft procedures are performed in approximately 600,000 patients annually. Although the use of autogenous vascular substitutes has had a major impact on advancing the field of reconstructive arterial surgery, these tissue sources may be inadequate or unavailable for widescale use. Moreover, their harvest adds time, cost and the potential for additional morbidity to the surgical procedure. These factors have led to the fabrication and use of synthetic vascular grafts. However, due to a high risk of thrombus formation none of these materials have proved suitable for generating small diameter grafts (less than 6 mm in diameter) useful for replacing the saphenous vein, internal mammary or radial artery for example. Various tissue engineering methods, including some using extracellular matrix (ECM) coating strategies, have emerged to address this issue but none have shown long-term reliable outcomes matching the characteristic native vasculature.

Extracellular matrix (ECM) forms the basis of the microenvironment within which cells exist in vivo, and as such, it communicates with and influences the behavior of those cells. The use of cell-derived ECM as a bioactive substrate for modulation of cell function has become an area of interest for many researchers. It is now well established in the art that chemical cross-linking of decellularized ECM can modulate cell function. Particularly, glutaraldehyde fixation or heat denaturation can reduce endothelial cell (EC)-derived ECM thrombogenicity and crosslinking of decellularized vein also results in decreased thrombogenicity. Presently, the process of ECM assembly and particularly the role of cells in a process driven by self-assembly and polymerization remain unclear. Collagen molecules might be involved in nucleating collagen fibrils, fibronectin and integrins to specify their site of assembly. Also non-collagenous molecules including N-propeptides of collagen, lysyl oxidase, tenascin-X, several proteoglycans, and thrombospondin-2 (TSP2) might influence the rate of assembly, size, and structure of collagen fibrils. Presently, the process of ECM assembly and particularly the role of cells in a process driven by self-assembly and polymerization remain unclear.

TSP2 is an anti-angiogenic, matricellular protein that has been shown to interact not only with ECM proteins, but also with a variety of cell surface receptors including CD36, CD47, heparin sulfate proteoglycan, low-density lipoprotein receptor-related protein, and $\alpha_v\beta_3$. Investigations on TSP2 Knock out (KO) mice have shown that TSP2 KO phenotype is dominated by abnormalities in connective tissue and a platelet aggregation defect which manifests an abnormal bleeding tendency. Previously, it was thought that the bleeding diathesis was due to irregular interactions of megakaryocytes with the vascular sinuses in the TSP2 KO bone marrow microenvironment, though more recent studies indicate a matrix defect is responsible. Furthermore, the interactions between collagenous ECM and the blood glycoprotein von Willebrand Factor (vWF) are critical for hemostasis and thrombosis. However, the key factors involved in the regulation of these interactions remain unknown.

There is a need in the art for compositions and methods for generating small vascular diameter grafts that prevent thrombogenicity while favoring angiogenesis. The present invention addresses this need.

SUMMARY OF THE INVENTION

The present invention relates to novel compositions and methods for reducing or eliminating the thrombogenicity of a graft by modifying the graft with a cell-derived extracellular matrix lacking thrombospondin-2 (TSP2-null ECM).

In one aspect, the invention includes a method of reducing the thrombogenicity of a graft. The method comprises modifying the graft with a cell-derived TSP2-null ECM.

In another aspect, the invention includes a method of eliminating the thrombogenicity of a graft. The method comprises modifying the graft with a cell-derived TSP2-null ECM.

In yet another aspect, the invention includes a method of rendering a graft pro-migratory, the method comprising modifying the graft with a cell-derived TSP2-null ECM, wherein, when implanted, the graft is re-endothelialized by the recipient's vascular endothelial cells.

In some embodiments, the TSP2-null ECM modified graft is less adhesive for blood glycoprotein von Willebrand Factor (vWF) as compared to a reference graft modified with an ECM not lacking TSP2. In other embodiments, the graft is at least one selected from the group consisting of an organ, a tissue and a vascular graft. In yet other embodiments, the vascular graft is a graft of 6 millimeters or less in diameter.

The invention additionally includes a method of transplanting a non-thrombogenic graft to a subject in need thereof. The method of the invention comprises administering to a subject in need thereof a graft modified with a cell-derived TSP2-null ECM.

The invention further includes a method for reducing or eliminating the risk of developing a thrombosis associated with graft transplant in a subject in need thereof. The method comprises modifying a graft to be transplanted into a subject with a cell-derived TSP2-null ECM, wherein the risk of developing a thrombosis in the transplanted subject is reduced or eliminated.

In some embodiments, a therapeutic agent in a pharmaceutically acceptable carrier is further administered to the subject. In other embodiments, the non-thrombogenic graft is pretreated with a therapeutic agent in a pharmaceutically acceptable carrier prior to being administered to the subject. In some embodiments, the subject is a human.

The invention also includes a method of improving the biocompatibility of a medical device or an implant, the method comprising modifying the medical device or implant with a cell-derived TSP2-null ECM, wherein the biocompatibility of the treated medical device or implant is improved.

The invention also includes a non-thrombogenic composition comprising a cell-derived TSP2-null ECM.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments, which are presently preferred. It should be understood, however, that the invention is not limited to the precise arrangements and instrumentalities of the embodiments shown in the drawings.

FIG. 1A: Rescue of irradiated WT and KO mice with KO and WT bone marrow cells, respectively, did not alter the bleeding time of the host. In addition, homotypic rescue maintained the original phenotype. Transplant of WT bone marrow to irradiated TSP2 KO mice did not reduce the bleeding time. FIGS. 1B-1C: Representative SEM images of denuded carotid arteries from WT (FIG. 1B) and TSP2 KO (FIG. 1C) mice 10 minutes after wire injury. FIG. 1D: Quantification of thrombus size by Image J revealed a decrease in TSP2 KO arteries. *p<0.05

FIGS. 2C-2D Representative images of WT (FIG. 2C) and TSP2 KO (FIG. 2D) aortic segments immunostained for PECAM-1 are shown and demonstrate lack of endothelium. Arrow in D denotes remnants of endothelium. FIGS. 2E-2F: Representative images of WT (FIG. 2E) and TSP2 KO (FIG. 2F) aortic segments immunostained for TSP2 are shown and demonstrate presence and absence of TSP2, respectively. Arrows in FIG. 2E denote TSP2 immunoreactive cells. FIGS. 2G-2H Representative images of immunofluorescence detection of vWF in WT (FIG. 2G) and TSP2 KO (FIG. 2H) aortic segments are shown (Zeiss, 10× objective). WT segments show excessive vWF immunoreactivity in the area of thrombus formation, which is absent in TSP2 KO grafts. * denotes lumen area and arrows the edge of the vessel. Sections were counterstained with methyl green (FIGS. 2A-2F) or DAPI (FIGS. 2G-2H). n=5.

FIGS. 3A-3C: Representative images of platelets visualized by rhodamine-phalloidin on WT (FIG. 3A) or TSP2 KO ECM (FIG. 3B) are shown. FIG. 3C shows detection of platelets and immunofluorescence detection of fibronectin in TSP2 KO ECM, which confirms the retention of ECM during the duration of the experiment (Zeiss, 40× objective). FIG. 3D: Quantification of platelet area by Image J showed reduced platelet aggregation on TSP2 KO ECM. n=5, *p<0.05

FIG. 4A: Representative images of immunofluorescence detection of several ECM components in fibroblast-derived decellularized WT and TSP2 KO ECM (Zeiss, 10× objective). FIGS. 4B-4C: Representative SEM images of WT (FIG. 4B) and TSP2 KO (FIG. 4C) decellularized ECM deposited on tissue culture plastic. Collagen fibril arrangement appeared less aligned in the latter (Hitachi, 20,000× magnification). FIG. 4D: PCR analysis of several ECM proteins expressed by WT and TSP2 KO dermal fibroblasts revealed similar levels of expression. FIG. 4E: Determination of ECM Young's Modulus by AFM. A 2 μm bead affixed to the end of an AFM cantilever was used to perform nanoindentation studies on WT and TSP2 KO ECM. After force curves were collected, Young's Modulus was determined using NanoScope Analysis Software. n=8. In addition, entire grafts underwent biomechanical analysis for various parameters. FIG. 4F: ECM modification/coating does not alter mechanical properties of grafts. Decellularized, unmodified/uncoated and ECM modified/coated (10 days) grafts were subjected to suture strength and INSTRON uniaxial testing. There were no differences found among the groups for suture strength (n=3), Young's modulus or ultimate tensile strength (n=6), indicating that the coating process does not affect the mechanical properties of the grafts.

(FIG. 5A, FIG. 5B) Immunofluorescence detection of fibronectin revealed retention of the ECM at the conclusion of the experiment. FIGS. 5C-5D: vWF accumulation on ECM was detected by immunofluorescence (Zeiss, 20× objective). Interaction with TSP-null ECM (FIG. 5D) was minimal in comparison to WT (FIG. 5C) and this was confirmed by image analysis using Image J (FIG. 5E). n=3, *p<0.05

FIGS. 6A-6B: Representative AFM approach and retract curves for adhesion of vWF-coated bead to WT ECM (FIG. 6A), where there is significant adhesion (denoted by the downward spike in the retract curve) and TSP2 KO ECM (FIG. 6B), where there is no visible adhesion. FIG. 6C: Quantification of the adhesion force was performed using NanoScope Analysis software and showed reduced on the TSP2 KO ECM. n=5, *p<0.05.

FIG. 7A: Representative image of a bead (arrow) immobilized to the tip of a cantilever. FIGS. 7B-7C: Representative image showing immunofluorescence detection of vWF on the tip of a cantilever carrying a vWF-conjugated bead (FIG. 7B). No vWF was detected on an unconjugated bead (FIG. 7C).

FIG. 11A: Fluorescent images show the lumen of decellularized aortas that were uncoated or coated for 10 days with WT ECM (to serve as controls) as well as aortas modified/coated with TSP2 KO ECM for 3-10 days. These grafts were then been subjected to platelet-rich plasma with shaking for 1 hour. FIG. 11B: Using MetaMorph® analytical software, the percent area of the graft covered with platelets was quantified for each of the conditions (n=5). While there was a trend toward decreased platelet adhesion with increased coating time, the difference between controls and TSP2 KO ECM modification/coating was not significant until day 10.

FIGS. 20A-20D: One month after bone marrow transplantation, TSP2-positive megakaryocytes were detected in WT recipients rescued with either WT (FIG. 20A) or TSP2 KO (FIG. 20B) bone marrow. In contrast, no TSP2 was detected in bone marrow of TSP2 KO recipients regardless of donor genotype (FIGS. 20C-20D). FIG. 20E: Analysis of platelet response to ADP revealed normal aggregation in PRP from WT mice rescued with either genotype and suboptimal aggregation in PRP from TSP2 KO mice rescued with either genotype.

DETAILED DESCRIPTION

Definitions

Figures 1A, 1B, 1C, 1D:
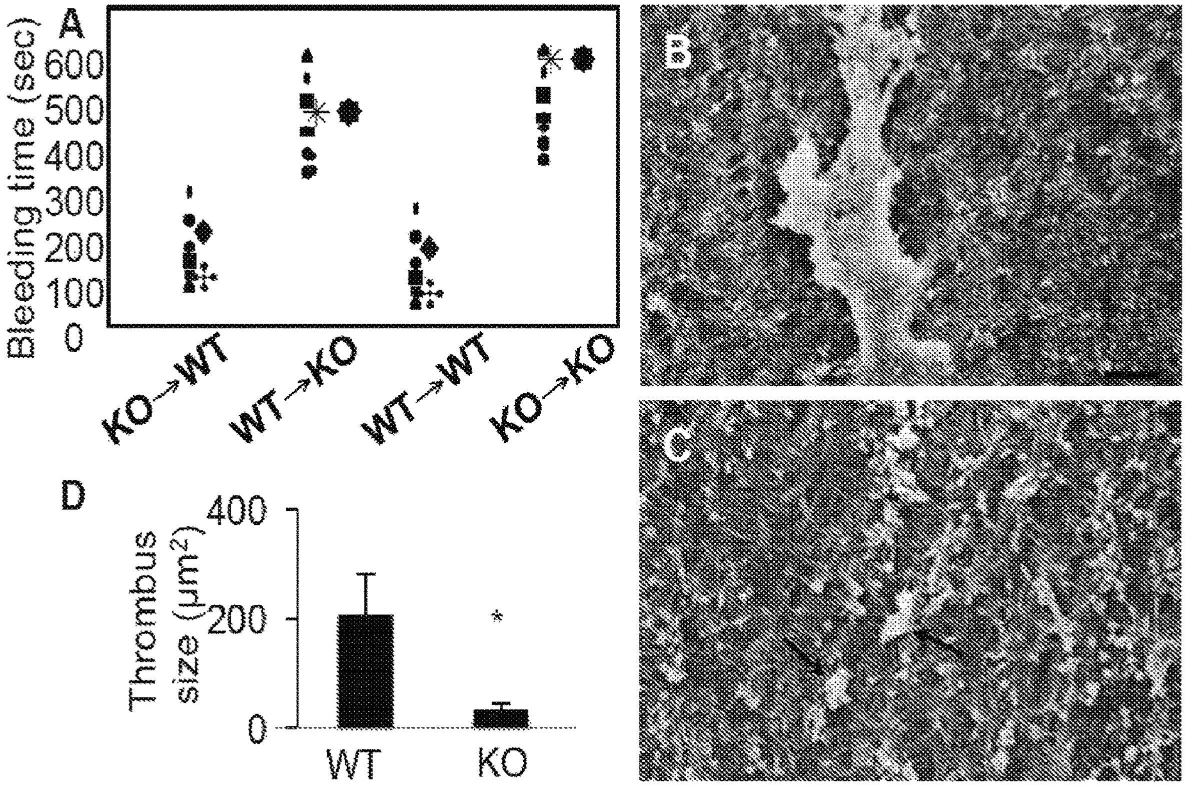
FIGS. 1A-1D are a series of graphs, images and histograms demonstrating that vessel ECM abnormality contributes to the bleeding diathesis in TSP2 KO mice.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

By "alteration" is meant a change (increase or decrease) in the expression levels or activity of a marker or clinical indicator as detected by standard art known methods such as those described herein. As used herein, an alteration includes a 10%-100% change in measured levels (e.g., 10, 20, 30, 40, 50, 60, 75, 80, 85, 90, 95, 100%).

The term "biocompatibility" refers to the properties of materials, such as a medical device or an implant, device being biologically compatible by not eliciting local or systemic responses from a living system or tissue.

The term "coating" refers to a covering, layer or film, of a substance applied to the surface of a substrate. The coating may be an all-over coating, completely covering the substrate, or it may only cover parts of the substrate. As used herein, "grafts' coating" refers specifically to grafts that are modified with a non-thrombogenic and pro-migratory cell-derived extracellular matrix (ECM), more specifically, the grafts used herein are modified with a cell-derived ECM that is genetically modified and lack thrombospondin-2 (TSP2-null ECM) also referred to as "TSP2 KO ECM".

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The expression "difference in the level of" or "differentially present" refers to differences in the quantity and/or the frequency of a marker present in a sample taken from subjects having a disease as compared to a control subject. A marker can be differentially present in terms of quantity, frequency or both. A difference in the level of a polypeptide is present between two samples if the amount of the polypeptide in one sample is statistically significantly different from the amount of the polypeptide in the other sample. Alternatively or additionally, a polypeptide is differentially present between two sets of samples if the frequency of detecting the polypeptide in a diseased subjects' samples is statistically significantly higher or lower than in the control samples. A marker that is present in one sample, but undetectable in another sample is differentially present.

A "disease" is a state of health of an animal wherein the animal cannot maintain homeostasis, and wherein if the disease is not ameliorated then the animal's health continues to deteriorate. "Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The terms "extracellular matrix" or "ECM" refer to proteins that are secreted by cells and assembled in a three dimensional manner to provide structural support for cells. Generally, extracellular matrix comprises proteins such as type I and V collagens, vitrogen, fibronectin, laminin, entactin, and nidogen; and glycosaminoglycans and proteoglycans. However, it is noted that the extracellular matrix can vary in molecular size, composition, and structural assembly, depending on its anatomic origin. In some instances, ECMs include an isolated basement membrane produced by vascular endothelial cells and a membrane on which the cells rest in vivo. Non limiting examples of ECMs are ones produced using fibroblasts (primary dermal fibroblasts, as well as cell lines MC3T3s and NIH3T3s) and primary smooth muscle cells. While matrices may differ somewhat in their composition, they are primarily composed of collagens (I, HI, IV, VI), fibronectin, laminins, and other matricellular proteins. Despite the variation due to anatomic origin, extracellular matrix from any anatomic site could be useful in the present invention. Of particular interest in the present invention, are ECMs that comprise extracellular molecules that form a three-dimensional structure supporting cell and tissue growth. The molecules and structure secreted by matrix-producing cells could be produced in in vitro.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical. The choice of using an extracellular matrix derived from the anatomic source of the same type as the graft to treat the graft according to the method of the present invention may be helpful in optimizing recolonization post-transplant, or seeding pretransplant, in a treated graft.

The term "immune response" as used herein is defined as a host response to an antigen that occurs when lymphocytes identify antigenic molecules as foreign and induce the formation of antibodies and/or activate lymphocytes to remove the antigen.

As used herein, the terms "immunosuppression" or "immunosuppressive therapy (IST)" involve an act that reduces the activation or efficacy of the immune system. Deliberately induced immunosuppression is performed to prevent the body from rejecting an organ transplant, treating graft-versus-host disease after a bone marrow transplant, or for the treatment of auto-immune diseases such as rheumatoid arthritis or Crohn's disease.

As used herein, the term "implant" refers to any metallic or non-metallic material inserted or grafted into the body. An implant can be used to maintain support and tissue contour for various bones or parts of the body such as the spine, femur, neck, knee, wrist, nose. Examples of implants include, but are not limited to, prosthetic joints, screws and plates.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

By "marker" is meant any protein or polynucleotide having an alteration in level or activity that is associated with a disease or disorder.

As used herein, the term "medical device" is a device used in a medical procedure. Non limiting examples of medical devices include, but are not limited to, vascular products, closure devices, heart valves, coils, catheters, stents, medical balloons, hollow components, tubes, catheter tips, tip extensions, catheter shafts, catheter tubes and guide wires.

By the term "modified" as used herein, is meant a changed state or structure of a molecule or cell of the invention. Molecules may be modified in many ways, including chemically, structurally, and functionally. Cells may be modified through the introduction of nucleic acids therein.

The term "model organism" refers to a non-human species that is easy to maintain and breed in a laboratory setting and has particular experimental advantages. Model organisms as used herein provide an in vivo model to research the effects of a human disease or condition and/or biological activities associated with a disease or condition, such as thrombosis.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Monitoring" refers to recording changes in a continuously varying parameter (e.g. monitoring progression of a disease).

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Non-thrombogenic" refers to a property of preventing blood coagulation.

"Parenteral" administration of an immunogenic composition includes, e.g., subcutaneous (s.c.), intravenous (i.v.), intramuscular (i.m.), or intrasternal injection, or infusion techniques.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The terms "purified", "biologically pure" or "isolated" as used herein mean having been increased in purity, wherein "purity" is a relative term, and not to be necessarily construed as absolute purity. For example, the purity of a substance, for example, but not limited to a nucleic acid, can be at least about 50%, can be greater than 60%, 70%, 80%, 90%, 95%, or can be 100%. The terms "purified", "biologically pure" or "isolated" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, "sample" or "biological sample" refers to anything, which may contain an analyte (e.g., polypeptide, polynucleotide, or fragment thereof) for which an analyte assay is desired. The sample may be a biological sample, such as a biological fluid or a biological tissue. In one embodiment, a biological sample is a salivary sample. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

By the term "specifically binds," as used herein with respect to an antigen binding molecule is meant an antigen binding molecule which recognizes a specific antigen, but does not substantially recognize or bind other molecules in a sample. For example, an antigen binding molecule that specifically binds to an antigen from one species may also bind to that antigen from one or more species. But, such cross-species reactivity does not itself alter the classification of an antigen binding molecule as specific. In another example, an antigen binding molecule that specifically binds to an antigen may also bind to different allelic forms of the antigen. However, such cross reactivity does not itself alter the classification of an antigen binding molecule as specific. In some instances, the terms "specific binding" or "specifically binding," can be used in reference to the interaction of an antigen binding molecule, an antibody, a protein, or a peptide with a second chemical species, to mean that the interaction is dependent upon the presence of a particular structure (e.g., an antigenic determinant or epitope) on the chemical species; for example, an antigen binding molecule or an antibody recognizes and binds to a specific protein structure rather than to proteins generally. If an antigen binding molecule is specific for epitope "A", the presence of a molecule containing epitope A (or free, unlabeled A), in a reaction containing labeled "A" and the antigen binding molecule, will reduce the amount of labeled A bound to the antigen binding molecule.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

As used herein, the term "transplantation" refers to the process of taking a cell, tissue, or organ, called a "transplant" or "graft" from one individual and placing it or them into a (usually) different individual. The individual who provides the transplant is called the "donor" and the individual who received the transplant is called the "host" (or "recipient"). An organ, or graft, transplanted between two genetically different individuals of the same species is called an "allograft". A graft transplanted between individuals of different species is called a "xenograft".

As used herein, "transplant rejection" refers to a functional and structural deterioration of the organ due to an active immune response expressed by the recipient, and independent of non-immunologic causes of organ dysfunction.

As used herein, the term "tolerance" is a state of immune unresponsiveness specific to a particular antigen or set of antigens induced by previous exposure to that antigen or set. Tolerance is generally accepted to be an active process and, in essence, a learning experience for T cells. Tolerance, as used herein, refers to the inhibition of a graft recipient's ability to mount an immune response which would otherwise occur, e.g., in response to the introduction of a nonself MHC antigen into the recipient. Tolerance can involve humoral, cellular, or both humoral and cellular responses.

To "treat" a disease as the term is used herein, means to reduce the frequency or severity of at least one sign or symptom of a disease or disorder experienced by a subject. It will be appreciated that, although not precluded, treating a disorder or condition does not require that the disorder, condition or symptoms associated therewith be completely eliminated.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to novel compositions and methods for reducing the thrombogenicity of a graft. This is accomplished by treating the graft with an extracellular matrix lacking thrombospondin-2 (TSP2-null ECM) to render it non-thrombogenic when transplanted to a subject in need thereof. The invention also provides a method of improving the biocompatibility of a medical device or an implant by coating the medical device or implant with TSP2-null ECM.

In one embodiment, the invention provides a non-thrombogenic composition for coating a graft by modifying the graft with a cell derived ECM. The composition comprises TSP2-null ECM. In some aspects, the composition of the invention composition is useful for modifying a graft to be transplanted in a subject in need thereof wherein the modification on the graft is achieved with a cell derived ECM and reduces the risk of subsequent thrombosis when the graft is transplanted into the subject.

In one embodiment, the method of the present invention comprises modifying the surface of a graft with TSP2-null ECM thereby rendering it non-thrombogenic.

In one embodiment, the invention provides a method for reducing or eliminating the risk of developing a thrombosis associated with graft transplant in a subject in need thereof, the method comprising modifying the graft with a TSP2-null ECM so that the risk of developing a thrombosis in the transplanted subject is reduced or eliminated.

Generation of TSP2-Null ECM

Obtaining ECM

In some embodiments, obtaining ECM is accomplished using methods known to those skilled in the art. In some instances, ECM can be obtained as an in vitro structure by isolating primary matrix-producing cells or plating matrix producing cells from established cell lines and culturing them in the presence of an acid solution, such as ascorbic acid, to aid in the excretion of collagen molecules for 3 to 10 days depending on the intended need thereof. A decellularization of the ECM is then performed via a short wash (2-10 minutes) with a basic wash solution (e.g. 40 mM ammonium hydroxide and 0.5% triton X-100) at a temperature range of 25° C. to 37° C. In some embodiments, the ECM is subsequently treated with Dnase to circumvent the possibility of genomic DNA contamination. Dnase treatment is generally performed at a temperature range of 25° C. to 37° C. for about 1 hour.

The ECM is the natural substrate on which cells migrate, proliferate, and differentiate. These components are linked in such a way that the resulting structure is tri-dimensional scaffolding in vivo. Thus, the ECM provides scaffolding, support and strength to cells grown on it, allowing those cells to differentiate and mediate physiologic responses. ECMs from different anatomic sites may vary in their ability to support and allow for proper differentiation of cells not from that respective anatomic site. Further, without wishing to be bound by any theory, the ECM should ideally be produced from cells derived from the same species as the recipient. Thus, if the recipient is a human, a preferred ECM is a matrix made from human vascular endothelial cells since it is the most natural surface for such endothelial cells; and provides matrix recognition domains and corresponding cell receptors specific for, and enhancing the growth of, human vascular endothelial cells which colonize and modify the graft subsequent to coating.

TSP2-Null ECM

Generation of a TSP2-null ECM can be accomplished in a number of ways. In some aspects, the absence of expression of the TSP2 gene in the ECM may result from a full or partial knock out of the TSP2 gene. Methods of gene knock out are well known in the art. Briefly, a gene knock out refers to a genetic technique in which one of an organism's genes is made inoperative. Knock out is accomplished through a combination of well-established molecular techniques. In general individual stem cells are genetically transfected with the DNA construct for the goal of creating a transgenic animal that has the altered gene. Embryonic stem cells are genetically transformed and inserted into early embryos. The resulting transgenic animals with the genetic alteration in their germline cells then pass the knock out to future generations. For instance, a knock out mouse refers to a mouse in which a gene or genes have been mutated such that the activity of the gene has been reduced or eliminated. Of particular interest for the present invention, the thrombospondin-2 (TSP2) gene is knocked out. In other aspects, TSP2 gene is knocked down using other molecular techniques known in the art such as, but not limited to, RNA interference (RNAi), small hairpin RNA (shRNA) and Clustered Regularly Interspaced Short Palindromic Repeats (CRISPRs)). Knocked down expression of TSP2 is useful for generation of TSP2-null ECM in mammals where knock out of TSP2 is not possible, e.g., in humans. Thus, the term "TSP2-null ECM" as used herein should be construed to mean ECM derived from a mammalian tissue where the mammal comprises a TSP2 knockout genotype as well as ECM derived from a mammalian tissue where expression of TSP2 in the tissue has been knocked down using any means available in the art. In the latter instance, expression of TSP2 may be diminished when compared with wild type expression, and/or may be eliminated altogether. In some aspects, the characteristics of a TSP2-null ECM produced by a TSP2 knock down are optimized and similar to the ones produced by a TSP2 knock out.

Characteristic of a TSP2-Null ECM Modified Graft

In the present invention, when a graft is modified with TSP2-null ECM, this modification provides a coating surface on the graft which enhances re-endothelialization. Further, the modification with the TSP2-null ECM of this invention provides a surface for re-endothelialization by the recipient's vascular endothelial cells posttransplantation, or by autologous or allogeneic vascular endothelial cells seeded onto the treated graft prior to transplantation. In either case, the vascular endothelial cells which grow onto the TSP2-null ECM coating of a treated graft provide an additional interface between the donor graft vascular endothelial cells and the recipient's immune surveillance mechanisms, for the purpose of avoiding thrombosis and preventing or minimizing the recognition of the graft as foreign and subsequent graft rejection. In some embodiments, the TSP2-null ECM coating is less adhesive for blood glycoprotein von Willebrand Factor (vWF) as compared to a reference wild-type ECM not lacking TSP2. The modification of a graft with TSP2-null ECM supports vascular endothelial cells colonization by promoting adhesion, regulating growth factor activity, modulating protease activity, and by directly activating intracellular second messenger systems. In some embodiments, an optimal TSP2-null ECM modification of a graft will render the modified surface of the graft: (a) non-thrombogenic (i.e. maintaining the viability and normal homeostasis in the coated donor endothelial cells); (b) pro-angiogenic, pro-migratory (i.e. supportive of, and efficiently promoting re-endothelialization); (c) nonimmunogenic (with respect to the recipient).

Graft

In some embodiments, the graft is at least one selected from the group consisting of an organ, a tissue and a vascular graft. In other embodiments, the vascular graft is a small diameter graft with an internal diameter of less than 10 millimeters (mm). In yet other embodiments, the vascular graft internal diameter is 9, 8, 7, 6, 5, 4, 3, 1 mm or less. The method of the invention particularly contemplates vascular grafts having an internal diameter of 6 millimeters (6 mm) or less.

Graft Preservation

In some aspects, the method of the invention comprises removing the graft to be transplanted from a donor, immediately decellularize it and store it in a sterile preservation solution such as 4% penicillin/streptomycin in PBS at 4° C. for up to 6 months before being used and modified with TSP2-null ECM.

In other aspects, the method of the invention comprises removing the graft to be transplanted from a donor, and preserving the removed graft so that it can be subsequently modified with TSP2-null ECM. In other aspects, the ex vivo preservation of the graft is accomplished using any preservation process known to those skilled in the art, including processes known for maintaining ongoing metabolism, for example, by pumping the graft with a perfusate composed of a highly enriched tissue culture medium which is supplemented with an oxygen carrier such as a perfluorochemical emulsion (U.S. patent application Ser. No. 08/033,629). In other aspects, according to the method of the invention, a graft to be transplanted is first removed from the donor and placed in a preservation solution. The preservation solution is a physiologically compatible solution to the graft, thereby maintaining graft cell viability and integrity. Essentially, the preservation solution may comprise a buffered salt solution supplemented with protein and/or other components helpful in maintaining cell viability or integrity. A basal cell culture medium may also be used as a preservation solution (known in the art such as M199, DMEM, etc.). Such cell culture medium may also be supplemented with other ingredients, such as, for example, with serum albumin. Other examples of a preservation solutions include a phosphate buffer with serum protein supplementation or serum substitute supplementation.

Medical Device or Implant Modified with TSP2-Null ECM

In one embodiment, the invention provides a method for improving the biocompatibility of a medical device or an implant by coating and modifying the medical device or implant with TSP2-null ECM, wherein the biocompatibility of the treated medical device or implant is improved and the medical device or implant is non-thrombogenic.

As used herein, "biocompatibility" refers to the measurement of the potential toxicity or immunological reaction in a subject or tissue resulting from bodily contact with a material or medical device. In some embodiments, the biocompatibility is measured in long-term implanted devices. In this instance, the biocompatibility of a long-term implantable medical device refers to the ability of the device to perform its intended function, with the desired degree of incorporation in the host, without eliciting any undesirable local or systemic effects in that host. In other embodiments, the biocompatibility is measured in short-term implantable devices. In this instance, the biocompatibility of a medical device that is intentionally placed within the cardiovascular system for transient diagnostic or therapeutic purposes refers to the ability of the device to carry out its intended function within flowing blood, with minimal interaction between device and blood that adversely affects device performance, and without inducing uncontrolled activation of cellular or plasma protein cascades. Yet in other embodiments, the biocompatibility is measured in tissue-engineering products. In this instance, the biocompatibility of a scaffold or matrix for a tissue-engineering products refers to the ability to perform as a substrate that will support the appropriate cellular activity, including the facilitation of molecular and mechanical signaling systems, in order to optimize tissue regeneration, without eliciting any undesirable effects in those cells, or inducing any undesirable local or systemic responses in the eventual host.

The present disclosure demonstrates that modifying a graft or a medical device or other implant with a TSP2-null ECM reduces various pathological aspects (e.g., thrombosis) associated with implantation into a host. Compositions and methods for reducing or ameliorating complications associated with implants in a mammal subject are provided also herein. Compositions and methods of the present invention are useful for treatment of mammals, and particularly humans.

Combination Therapies

The TSP2-null ECM compound described herein is also useful when combined with at least one additional compound. The additional compound may comprise commercially available compounds known to treat, prevent, or reduce the symptoms associated with graft transplants or implantation of a device into a subject.

In one aspect, the present invention contemplates that the TSP2-null ECM coating of the invention may be used in combination with a therapeutic agent such as an immunosuppressive agent. Non-limiting examples of immunosuppressive agents known in the art are cyclosporine, azathioprine, everolimus and glucocorticoids.

Pharmaceutical Compositions and Formulations.

The invention includes the use of a pharmaceutical composition combined with the TSP2-null ECM preparation as described herein for use in the methods of the invention.

Such a pharmaceutical composition is in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions are formulated using one or more pharmaceutically acceptable excipients or carriers. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences, 1991, Mack Publication Co., New Jersey.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Administration/Dosing

The regimen of administration may affect what constitutes an effective amount. For example, the therapeutic formulations may be administered to the patient either prior to or after a surgical intervention related to graft transplant or shortly after the patient receives a graft or other implant. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject (being a patient), preferably a mammal, more preferably a human, may be carried out using known procedures, at dosages and for periods of time effective to treat graft transplant in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the animal. Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient. A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of graft transplant in a patient.

Routes of Administration

One skilled in the art will recognize that although more than one route can be used for administration, a particular route can provide a more immediate and more effective reaction than another route.

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration. Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

In one embodiment, the administration route is a continuous subcutaneous administration for at least 2 days. In another embodiment, the administration route is a continuous subcutaneous administration for at least 20 days. In yet another embodiment, the administration route is a continuous subcutaneous administration for at least 30 days.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, which are adapted for controlled-release, are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Animals:

TSP2 KO and littermate WT (C57BL6/129SVJ) mice aged 3 to 4 months were used for these studies.

Bone Marrow Transplant:

WT and TSP2 KO mice were lethally irradiated (800 cGy) and rescued 24 hrs later with single cell suspensions of $5\times10^6$ donor bone marrow cells in prewarmed Hanks Balanced Salt Solution via tail vein injection (n=5/group). Recipient animals were studied 4 weeks post transplantation.

Bleeding Time:

Bleeding time was measured as described previously (Kyriakides et al, The Journal of Cell Biology. 1998; 140 (2):419-430).

Arterial Denudation:

Carotid arteries in mice that received bone marrow transplants were denuded of endothelium using nylon thread as described previously (Kyriakides et al., Blood. 2003; 101 (10):3915-3923). After 10 minutes, carotid arteries were fixed by perfusion, harvested, washed gently with phosphate buffered saline (PBS), and fixed overnight in 2% paraformaldehyde (paraformaldehyde) in 0.1M cacodylate buffer (Electron Microscopy Sciences) for scanning electron microscopy (SEM).

To further examine the anti-thrombotic potential of the TSP2 KO matrix, 2 mm sections of abdominal aorta from WT and TSP2 KO 8-12 week old mice were denuded of endothelium with nylon thread and interposed into the abdominal aortas of WT mice using an end-to-end anastomotic surgical technique as described previously (Yu et al., Circ Res. 2011; 109(4):418-427). After 48 hours (or earlier if in extremis), mice were anesthetized, perfused via the left ventricle, and the abdominal aortas were procured and fixed (4% paraformaldehyde) for histology.

Image Analysis:

Thrombus area and percent area covered by platelets were determined by image analysis with ImageJ.

Preparation of TSP2 KO ECM:

Dermal fibroblasts from WT and TSP2 KO mice were isolated and plated into 24-well plates, and decellularized as described previously (Krady et al., Am J Pathol. 2008; 173(3):879-891).

Platelet and VWF Studies:

Platelet rich plasma (PRP) or platelet poor plasma (PPP) were isolated and prepared as described previously (Kyriakides et al., Blood. 2003; 101(10):3915-3923). Platelet adhesion and activation on WT and TSP2 KO ECM was examined by pipetting PRP or platelets onto decellularized matrix. Matrix and plasma were allowed to interact for 30 minutes with shaking at 37° C. WT and TSP2 KO PPP were used to determine vWF levels via an ELISA (ThermoFisher). ADP aggregation experiments were performed as described previously (Kyriakides et al., Blood. 2003; 101(10):3915-3923).

Flow Chamber Studies:

WT and TSP2 KO matrices were produced on glass slides that could be placed in a flow chamber. In order to prepare matrices on slides, glass slides were placed in 1M NaOH for 1 hour, rinsed with deionized water, and allowed to air dry. Slides were subsequently autoclaved and coated with 1% gelatin before seeding with 250,000 cells each. Cells were cultured and matrix was prepared as described above.

Matrix-coated slides were placed in a flow chamber as described previously (Yoo et al., J Surg Res. 2007; 143(1): 94-98). Briefly, human plasma was flowed over slides for 0, 5, or 15 minutes at 15 dynes/cm$^2$. Once flow was stopped, slides were collected, washed with PBS, and fixed with 4% paraformaldehyde (pfa).

Histology, Immunohistochemistry, and Electron Microscopy:

Tissue samples: All tissue samples collected and fixed for histology during this study were paraffin embedded, sectioned, and mounted on glass slides. For initial visualization, tissues were stained with hematoxylin and eosin according to standard procedures. Immunolocalization of TSP-2 and PECAM-1 was performed as described previously (Krady et al., Am J Pathol. 2008; 173(3):879-891; Kyriakides et al, The Journal of Cell Biology. 1998; 140(2):419-430). Immunolocalization of vWF was performed after similar dewaxing and rehydration steps, but blocking was performed using 1% BSA in PBS for 30 minutes and then sections were incubated with FITC-conjugated vWF antibody (1:50 dilution; Abcam) and DAPI (1:1000 dilution; Invitrogen) for 30 minutes before mounting for fluorescent microscopy. Images were taken using Zeiss Axiovert 200 microscopes equipped with digital cameras.

All tissue samples collected for SEM during this study were fixed with 2% paraformaldehyde in 0.1M cacodylate buffer. After fixing, samples were dehydrated through an ethanol gradient and placed in hexamethyldisilazane (HMDS). Samples were allowed to air dry, and then were sputter coated with chromium and viewed via SEM (Hitachi SU-70).

In vitro studies: Immunofluorescent examination of ECM proteins was performed on decellularized WT and TSP2 KO ECM deposited in 24-well plates. After decellularization, ECM was fixed (4% paraformaldehyde), washed (PBS), and blocked (1% BSA in PBS) for 30 minutes. ECM was then incubated with antibodies to either collagen I (1:100, Abcam), collagen III (1:100, Abcam), collagen IV (1:400, Abcam), collagen VI (1:100, Abcam), fibronectin (1:100, Abcam), laminin (1:50, Abcam) or decorin (1:20, R&D Systems) overnight at 4° C. Wells were then washed (PBS) and incubated with secondary antibody (1:200; Invitrogen) for 30 minutes at room temperature. Wells were washed (PBS) and mounted (Vectashield Vector Labs) for fluorescent microscopy.

Reverse transcriptase-polymerase chain reaction (RT-PCR) was performed on WT and TSP2 KO cells grown in ECM-producing conditions for 10 days before lysing the cells in RIPA buffer. RNA was isolated from cells using an RNeasy kit (Qiagen) and reverse transcribed using QuantiTect Reverse Transcription Kit (Qiagen). PCR amplification was performed using primers for collagens I, III, IV, V, VI, fibronectin, or decorin. Amplification of RPLP0 (ribosomal protein, large, P0) served as a control. See Table 1 below for primer sequences.

Atomic Force Microscopy:

Sample preparation: ECM samples were prepared as described above on 8-well chamber slides (Nunc). Similarly, slides were coated with TSP1, TSP2 (R&D Systems), or collagen type I (BD Biosciences) by incubating 10 μg/mL purified protein in PBS at 4° C. overnight. Samples to be analyzed by atomic force microscopy (AFM) were also treated with 1% BSA in PBS to prevent non-specific binding to tissue culture plastic. Slides coated with pure protein were stained via immunofluoresence after AFM to ensure protein coverage and retention.

Figures 7A, 7B, 7C:
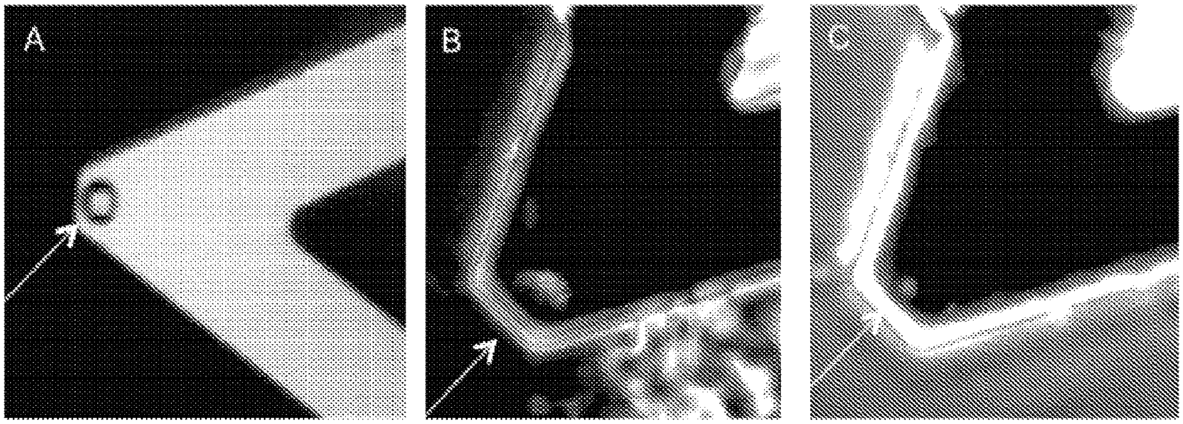
FIGS. 7A-7C are a series of images depicting the preparation of vWF-coated beads on AFM cantilevers. vWF was adhered to 2 μm beads which were then attached to AFM cantilever tips.

Cantilever preparation: Carboxylated polystyrene beads 2 μm in diameter (Invitrogen) were attached to tipless cantilevers (Bruker, NP-010) with UV-curing adhesive (Norland Products) using a micromanipulator. Recombinant vWF (Millipore) was subsequently conjugated via EDC/NHS chemistry to the beads on cantilevers. Bead attachment and vWF conjugation were confirmed via light and fluorescent microscopy, respectively (FIGS. 7A-7C).

Force Measurements: A Bruker Dimension Icon AFM was used to collect indentation curves to determine modulus and adhesion force. All measurements were performed using a fluid tip holder in 0.2×PBS. Cantilever calibration was performed before each set of measurements by analyzing force curves generated by cantilevers on a standard fused silica sample (Bruker) using the Nanoscope Analysis software to calculate deflection sensitivity. The thermal tune function of the Dimension AFM software was then used to calculate the cantilever's spring constant. For each sample, 15-20 force curves were collected at 2-3 areas selected for force measurements using a ramp rate of 0.5 Hz and a trigger threshold equivalent to the application of 2 nN of force. Force curves were analyzed for Young's Modulus (n=8) and adhesion force (n=5) using Nanoscope Analysis software.

TABLE 1

DNA sequences used for Q-PCR of ECM proteins

| ECM Component | Forward | Reverse |
|---|---|---|
| Collagen I | TGACTGGAAGAGCGGAGAGTACT (SEQ ID NO: 1) | CCTTGATGGCGTCCAGGTT (SEQ ID NO: 2) |
| Collagen III | CTGTAACATGGAAACTGGGGAAA (SEQ ID NO: 3) | CCATAGCTGAACTGAAAACCACC (SEQ ID NO: 4) |
| Collagen IV | AACAACGTCTGCAACTTCGC (SEQ ID NO: 5) | CTTCACAAACCGCACACCTG (SEQ ID NO: 6) |
| Collagen V | CTTCGCCGCTACTCCTGTTC (SEQ ID NO: 7) | CCCTGAGGGCAAATTGTGAAAA (SEQ ID NO: 8) |
| Collagen VI | CTGCTGCTACAAGCCTGCT (SEQ ID NO: 9) | CCCCATAAGGTTTCAGCCTCA (SEQ ID NO: 10) |
| Fibronectin | GAGAGGAGCACTACCCCAGA (SEQ ID NO: 11) | GCCCGGATTAAGGTTGGTGA (SEQ ID NO: 12) |
| Decorin | AATGTGGGTGTCAGCTGGAT (SEQ ID NO: 13) | CTAGCAAGGTTGTGTCGGGT (SEQ ID NO: 14) |

Platelet adhesion was examined by immunofluorescence. Briefly, non-adherent platelets were removed via PBS wash, fixed (4% paraformaldehyde), and stained with rhodamine-phalloidin (1:100, Molecular Probes) according to standard procedures.

For flow studies, immunolocalization was performed on fixed slides. To confirm retention of matrix under flow conditions, slides were placed in a blocking solution containing 1% BSA for 30 minutes and then incubated with an anti-fibronectin antibody (1:100, Abcam) for 2 hours. After washing (PBS), slides were incubated with a FITC-conjugated secondary antibody (1:200, Invitrogen) for 30 minutes and then washed and mounted for fluorescent microscopy. In order to examine the interaction of vWF with decellularized matrices, some slides were blocked in a blocking solution containing 1% BSA for 30 minutes and then sections were incubated with FITC-conjugated vWF antibody (1:50, Abcam) for 30 minutes before washing (PBS) and mounting for fluorescent microscopy. Images were taken using Zeiss microscopes equipped with a digital camera.

Statistical Analysis:

All data presented are expressed as means±standard error of the mean. Statistical differences were determined by either Student's t-tests or one-way ANOVA. A value of $P<0.05$ was considered to be significant.

The results of the experiments are now described in the following examples.

Example 1: Defective TSP2 KO ECM Contributes to the Bleeding Diathesis

It was previously reported a bleeding diathesis in TSP2 KO mice and that platelets isolated from TSP2 KO mice displayed suboptimal aggregation in vitro in response to ADP (Kyriakides et al., Blood. 2003; 101(10):3915-3923). In order to determine if the platelet defect was solely responsible for the bleeding diathesis, adoptive bone marrow transfers were performed. Both WT and TSP2 KO mice were irradiated and rescued with bone marrow from either WT or TSP2 KO donors. Successful transplantation was confirmed by detection of the WT and KO allele in KO and WT mice, respectively. One month after transplantation, TSP2-positive megakaryocytes were detected in WT recipients rescued with either WT or TSP2 KO bone marrow suggesting that irradiation-resistant MSCs remain a source for the protein (FIGS. 20A-20E). In contrast, TSP2 was undetected in bone marrow of TSP2 KO recipients regardless of donor genotype. In addition, analysis of platelet response to ADP revealed normal aggregation in PRP from WT mice rescued with either genotype, and suboptimal aggregation in PRP from TSP2 KO mice rescued with either genotype (FIGS. 20A-20E). Furthermore, the platelet numbers was assessed and no differences were found among any of the groups (WT→KO 730,000±85,498, KO→WT 601,000±68,636, WT→WT 698,000±53,609, KO→KO 726,000±75,208), nor among previously reported platelet counts of WT and TSP2 KO mice (Kyriakides et al., The Journal of Cell Biology. 1998; 140(2):419-430). To exclude the possibility that vWF levels could differ between WT and TSP2 KO mice, a vWF ELISA was performed and no differences were found (27.97±0.45 ng/mL for WT and 28.61±0.61 ng/mL for TSP2 KO; n=3). Bleeding times were determined and it was found that WT mice receiving WT and TSP2 KO bone marrow had bleeding times that did not differ from each other, nor from those of previously reported untransplanted WT mice (132 seconds) (Kyriakides et al., The Journal of Cell Biology. 1998; 140(2):419-430). In contrast, TSP2 KO mice receiving WT and TSP2 KO bone marrow had longer bleeding times, comparable to those of untransplanted TSP2 KO mice (552 seconds) (FIG. 1A).

In order to probe this defect further, the endothelium of the carotid arteries was denuded in bone marrow transplanted WT and TSP2 KO mice. Thrombus formation was greater in WT mice that were rescued with TSP2 KO marrow (FIG. 1B) versus TSP2 KO mice that were rescued with WT marrow (FIG. 1C). Image analysis confirmed that thrombus area was significantly increased in WT mice (FIG. 1D). These observations are consistent with a role for TSP2 in megakaryocyte function and production of normal platelets.

Example 2: Denuded TSP2 KO Arteries do not Cause Thrombosis

Figures 2A, 2B, 2C, 2D:
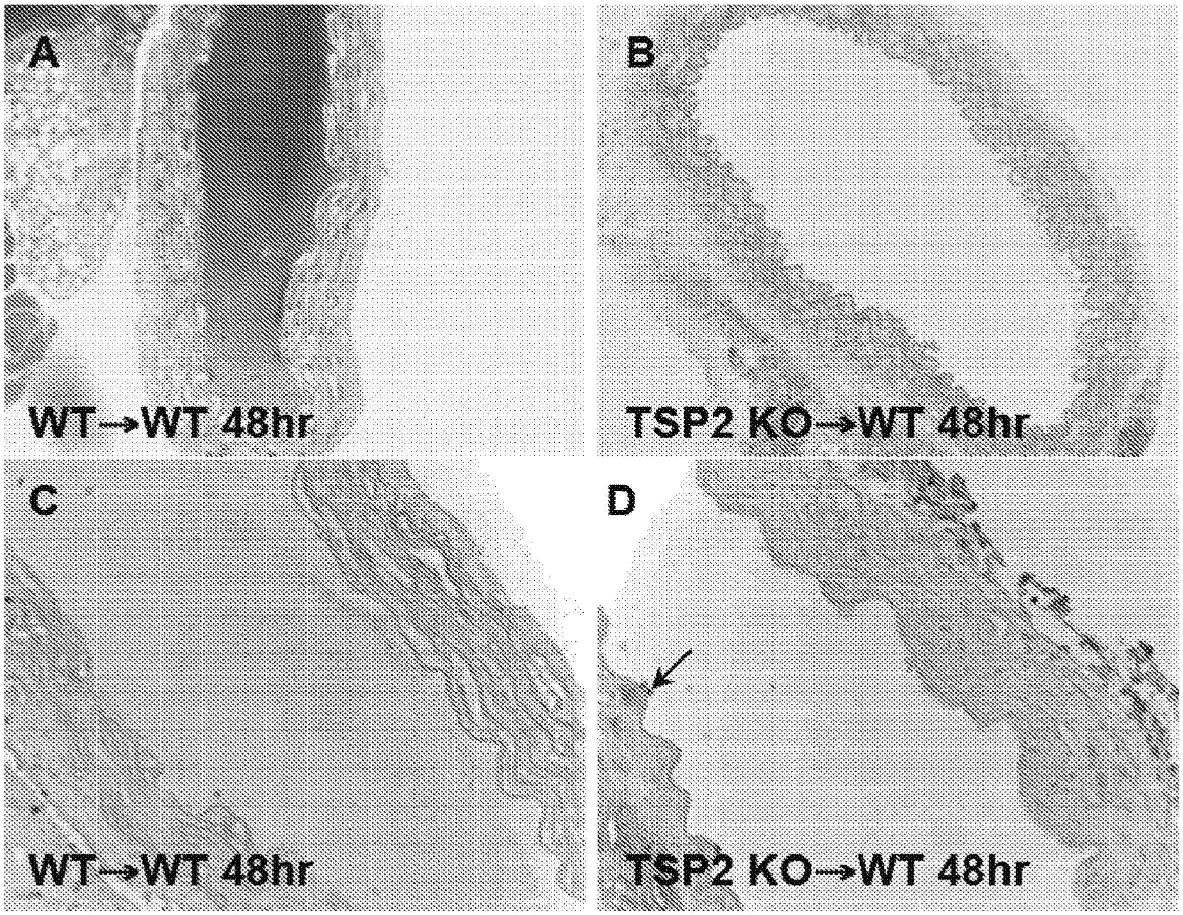
FIGS. 2A-2H are a series of images demonstrating that TSP2-null denuded aortic grafts resist thrombosis. Aortic segments from WT and TSP2 KO mice were denuded and grafted in WT mice. Representative images of H&E-stained sections of grafts 48 hr following surgery are shown. WT to WT graft (FIG. 2A) is completely occluded whereas the KO to WT graft is fully patent (FIG. 2B) (Zeiss, 4× objective).
Figures 2E, 2F, 2G, 2H:
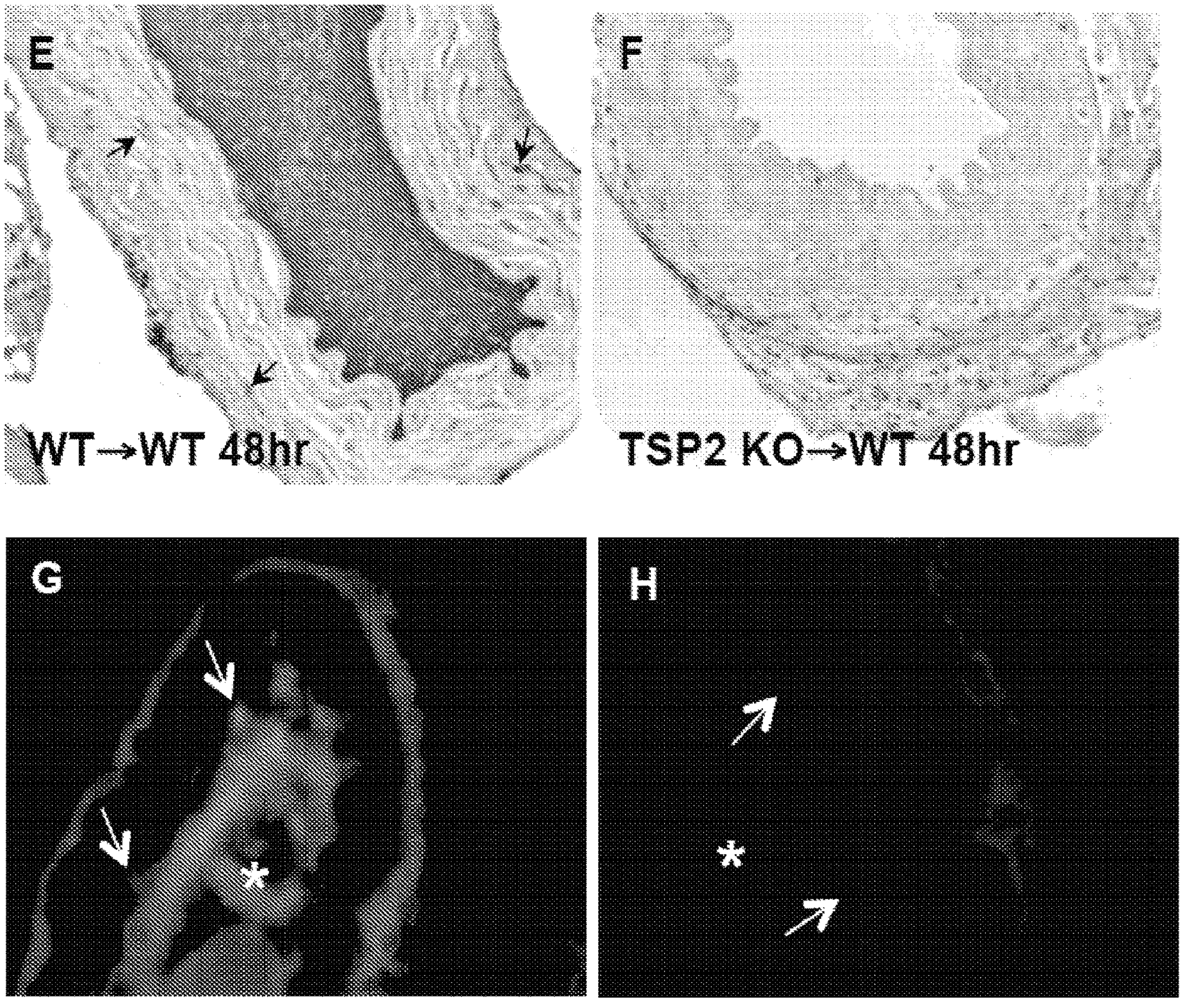

The results of the carotid artery denudations led to question whether the result could be recapitulated in an artery transplant model. In order to accomplish this, segments of aortas from either WT or TSP2 KO were removed from donor animals, denuded of endothelium, and grafted into the abdominal aortas of WT mice. WT to WT grafts were all occluded and resulted in the death of all animals within 48 hours (n=5) (FIG. 2A). WT recipients receiving TSP2 KO grafts, however, were all alive and the aorta grafts showed no signs of thrombus at 48 hours (n=5) (FIG. 2B). PECAM-1 staining confirmed the absence of endothelial cells in the denuded grafts (FIGS. 2C-2D). TSP2 staining clearly demonstrated that TSP2 KO grafts did not contain TSP2, while TSP2 is present in WT grafts (FIGS. 2F-2E, respectively). Immunofluorescence for vWF showed a decrease in the amount of vWF bound to TSP2 KO ECM in comparison to WT ECM (FIGS. 2H-2G). Because all graft recipients were WT animals, platelets and vWF levels were not variables in these experiments. Therefore, the results suggest that TSP2 KO ECM does not support normal platelet aggregation and this defect, in addition to platelet abnormalities, could play a significant role in their bleeding phenotype.

Example 3: Reduced Thrombogenicity of TSP2 KO ECM

Figures 3A, 3B, 3C, 3D:
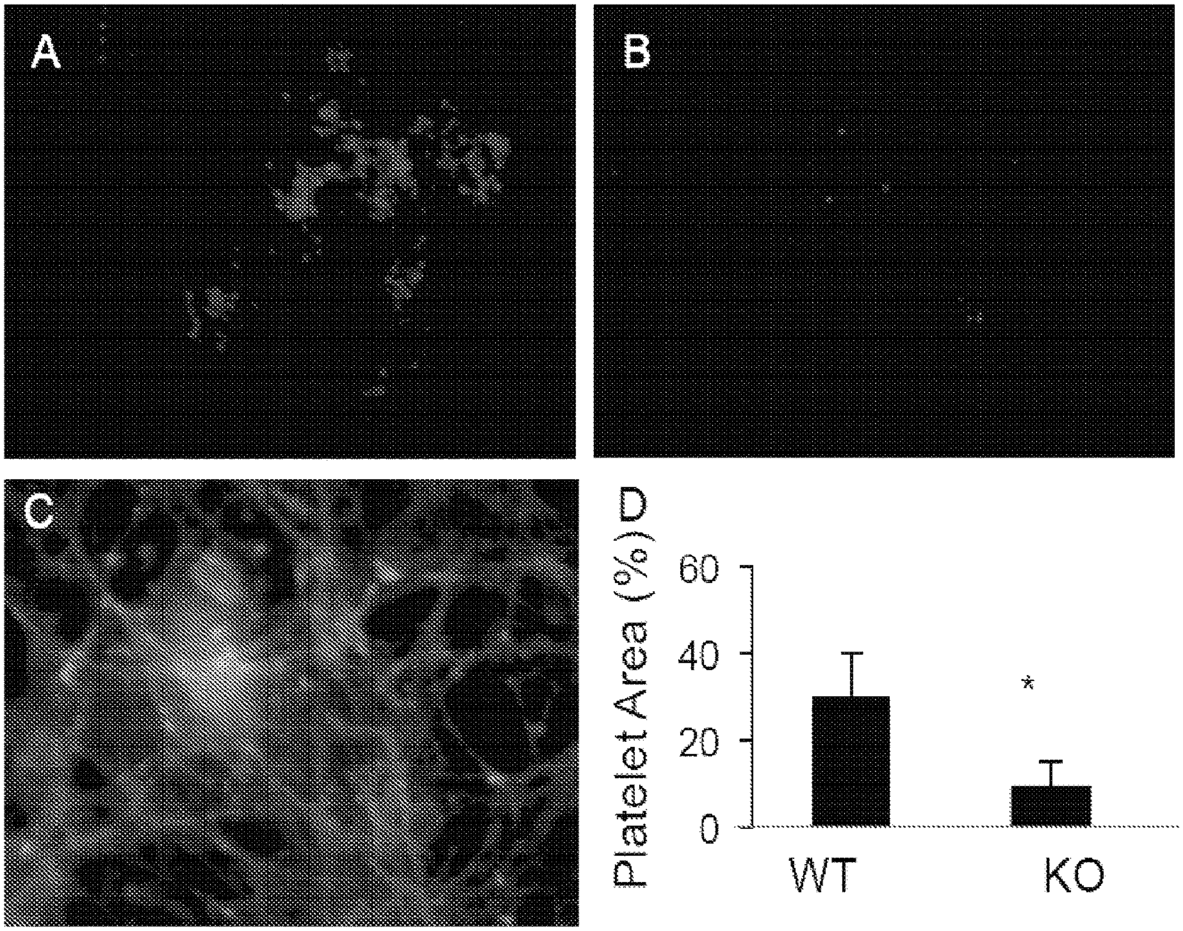
FIGS. 3A-3D are a series of images and histograms demonstrating that cell-derived TSP2 KO ECM does not support platelet aggregation. Fibroblast-derived ECM was prepared in vitro following decellularization of long-term (7 days) cultures. Mouse platelets were exposed to either WT or TSP2 ECM for 30 min at RT.

In order to study the interaction between platelets and TSP2 KO matrix in a more defined environment and determine whether the phenotype was retained in vitro, a decellularized dermal fibroblast-derived ECM from WT and from TSP2 KO cells were prepared and evaluated the ability of each to support platelet aggregation. PRP from WT mice ($1\times10^7$ platelets/mL) was added to wells containing either WT or TSP2 KO ECM. Platelets and ECM were allowed to interact for up to 30 minutes at 37° C. before fixing for fluorescence analysis. Fluorescence showed an increased number of platelets and aggregates on the WT ECM (FIG. 3A). In contrast, platelet adhesion was sparse with no aggregate formation on TSP2 KO ECM (FIG. 3B). Co-staining for FN verified ECM retention and that platelet adhesion was specific to ECM (FIG. 3C). Analysis of platelet fluorescence indicated a decrease percentage in the area of the image occupied by platelets on TSP2 KO ECM (FIG. 3D). These results indicate that platelets become activated on WT ECM but to a lesser degree on TSP2 KO ECM produced in vitro. It was previously shown that TSP2 is retained in decellularized WT ECM (Morris et al., Matrix Biol. 2014; 37:183-191). To examine whether it contributes to platelet adhesion, TSP2 KO ECM was treated overnight with 5 μg/ml TSP2 and then exposed to platelets. Despite detection of TSP2 on the KO ECM, platelet aggregation was not evident indicating that it does not directly influence this process (FIG. 3D).

Figures 4A, 4B, 4C:
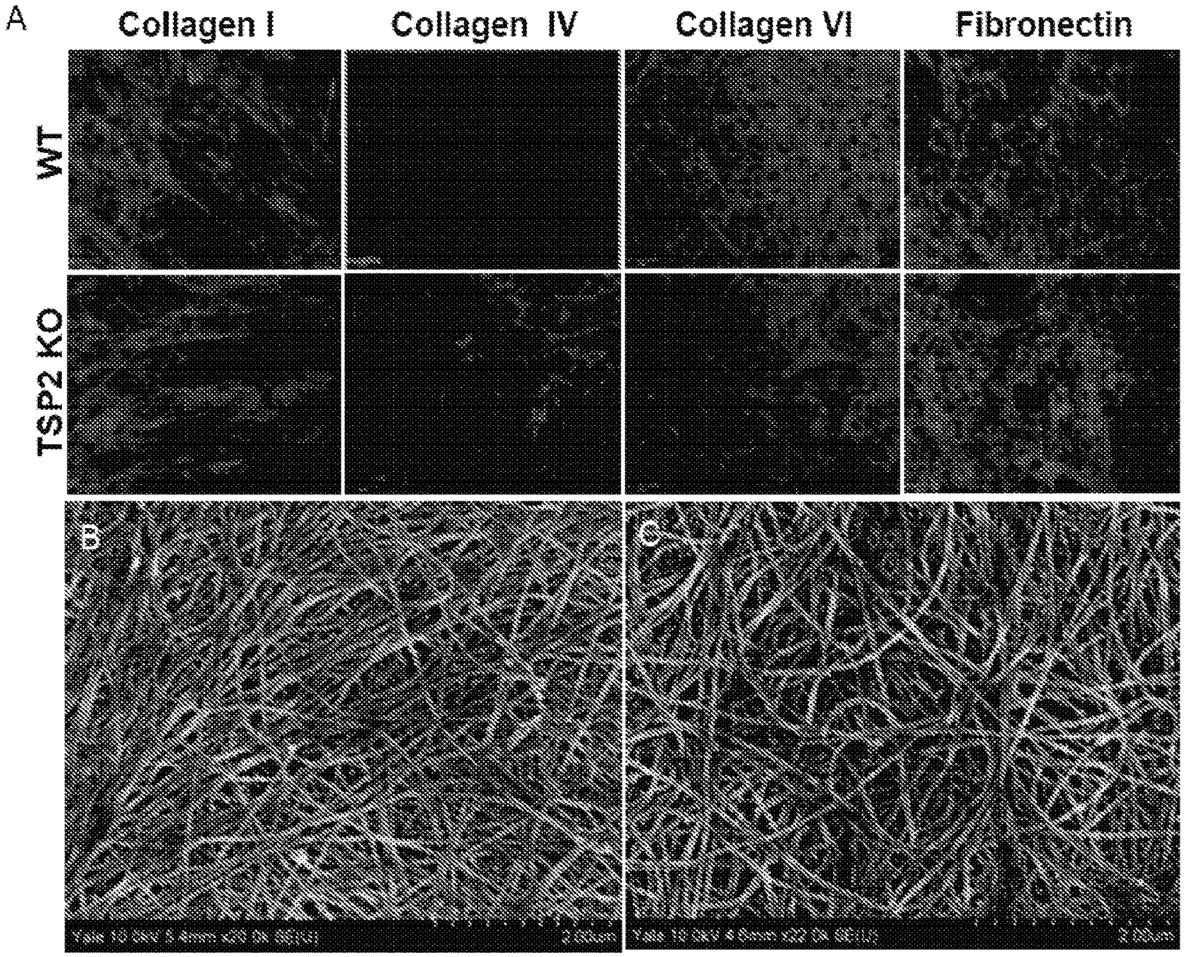
FIGS. 4A-4F are a series of images and histograms demonstrating that analysis of protein expression, deposition and ECM mechanical properties.
Figure 4D:
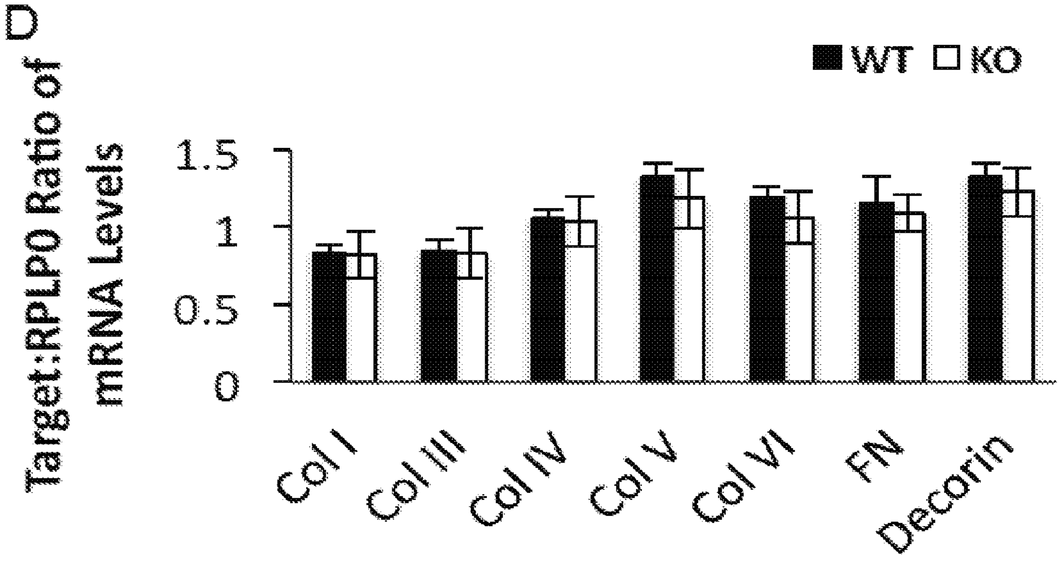
Figure 8:
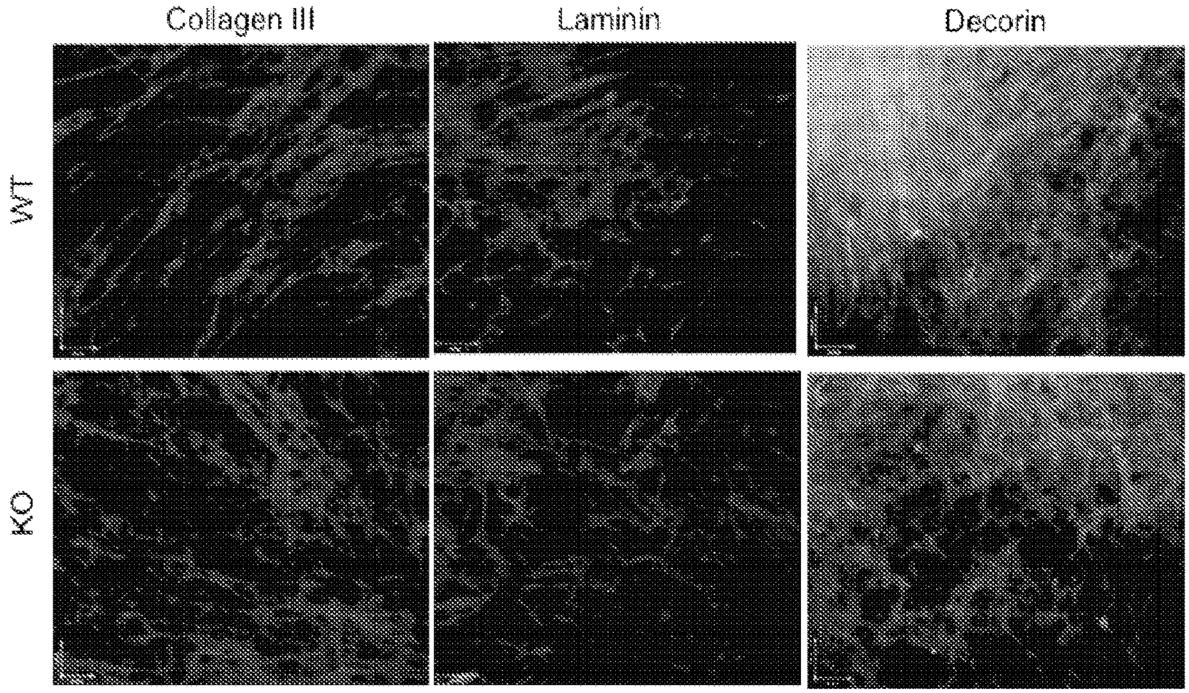
FIG. 8 is an image depicting immunofluorescence detection of Col3, laminin, and decorin in WT and TSP2 KO decellularized ECM.
Figure 9:
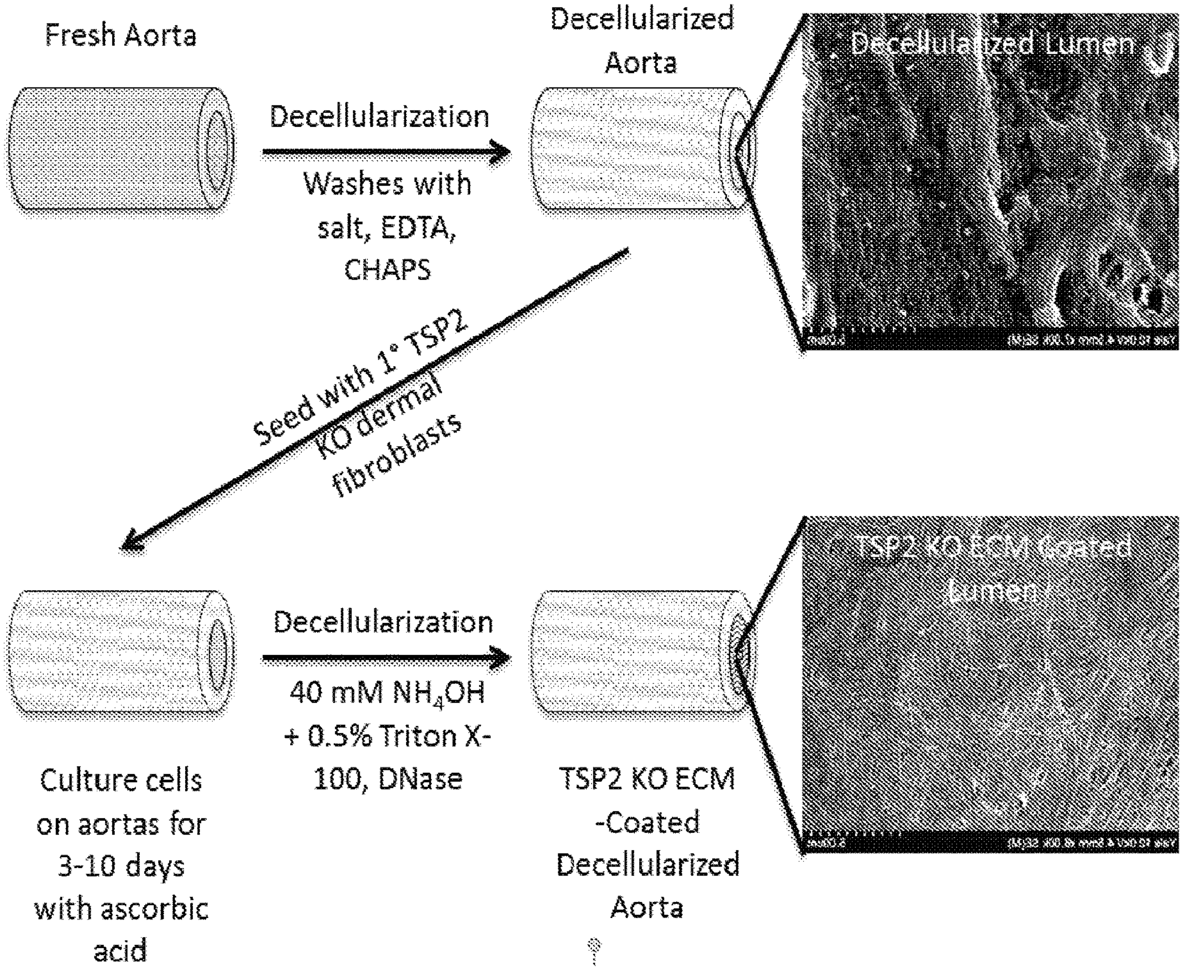
FIG. 9 is a series of drawings and images illustrating the production of decellularized, TSP2 KO ECM modified aortic grafts. Fresh aortic segments isolated from rat donor animals were thoroughly decellularized via an extensive process involving washes with salts, EDTA, and CHAPS. The top scanning electron microscope (SEM) image shows the uncoated lumen of the decellularized aorta. Once completely decellularized, the aorta lumens were seeded with TSP2 KO dermal fibroblasts, which were allowed to attach and produce ECM (in the presence of ascorbic acid) for 3-10 days. After the allotted time had elapsed, the grafts were subjected to a second, gentle decellularization, this time involving treatment with 40 mM ammonium hydroxide and 0.5% triton X-100, as well as a Dnase treatment. The lumen of the resulting graft after 10-day ECM production is shown in the bottom SEM image. The stark contrast in appearance is a good indication of complete ECM coating.
Figure 10:
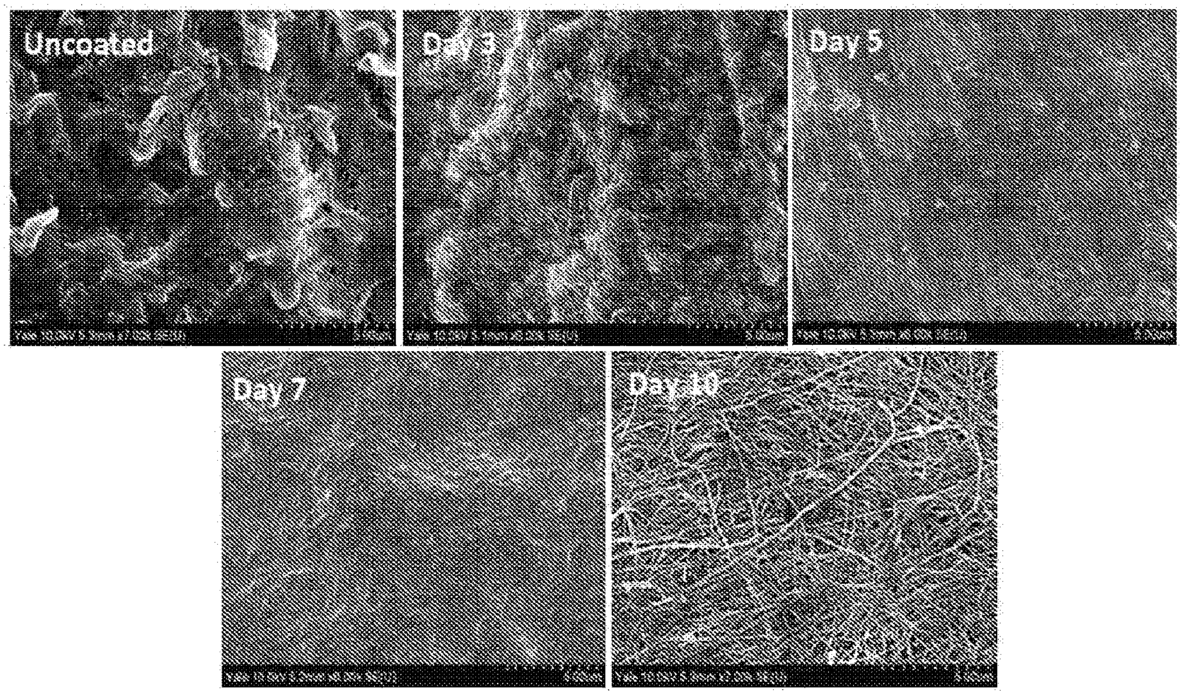
FIG. 10 is a series of images depicting the TSP2 KO ECM deposition over time. SEM images show the lumen of decellularized rat aortas modified with TSP2 KO ECM for 3-10 days. The 3-day modification/coating looks most immature, with native topography still visible below the thin TSP2 KO ECM modification/coating. Day 10 ECM looks most mature, though days 5 and 7 appear to mask the native topography well.
Figures 11A, 11B:
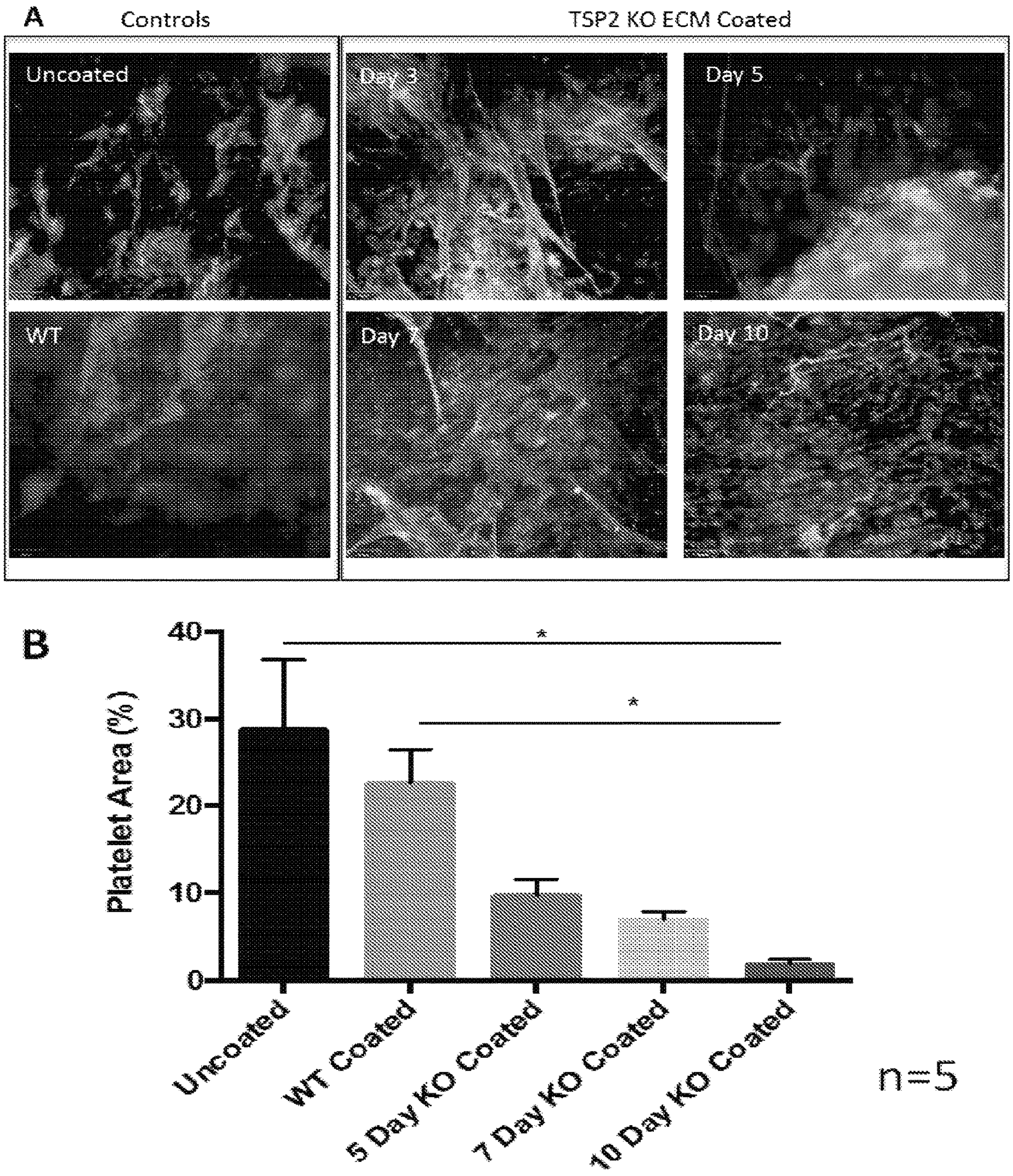
FIGS. 11A-11B are a series of images and histograms illustrating the immunofluorescent evaluation of coatings in vitro.
Figure 12:
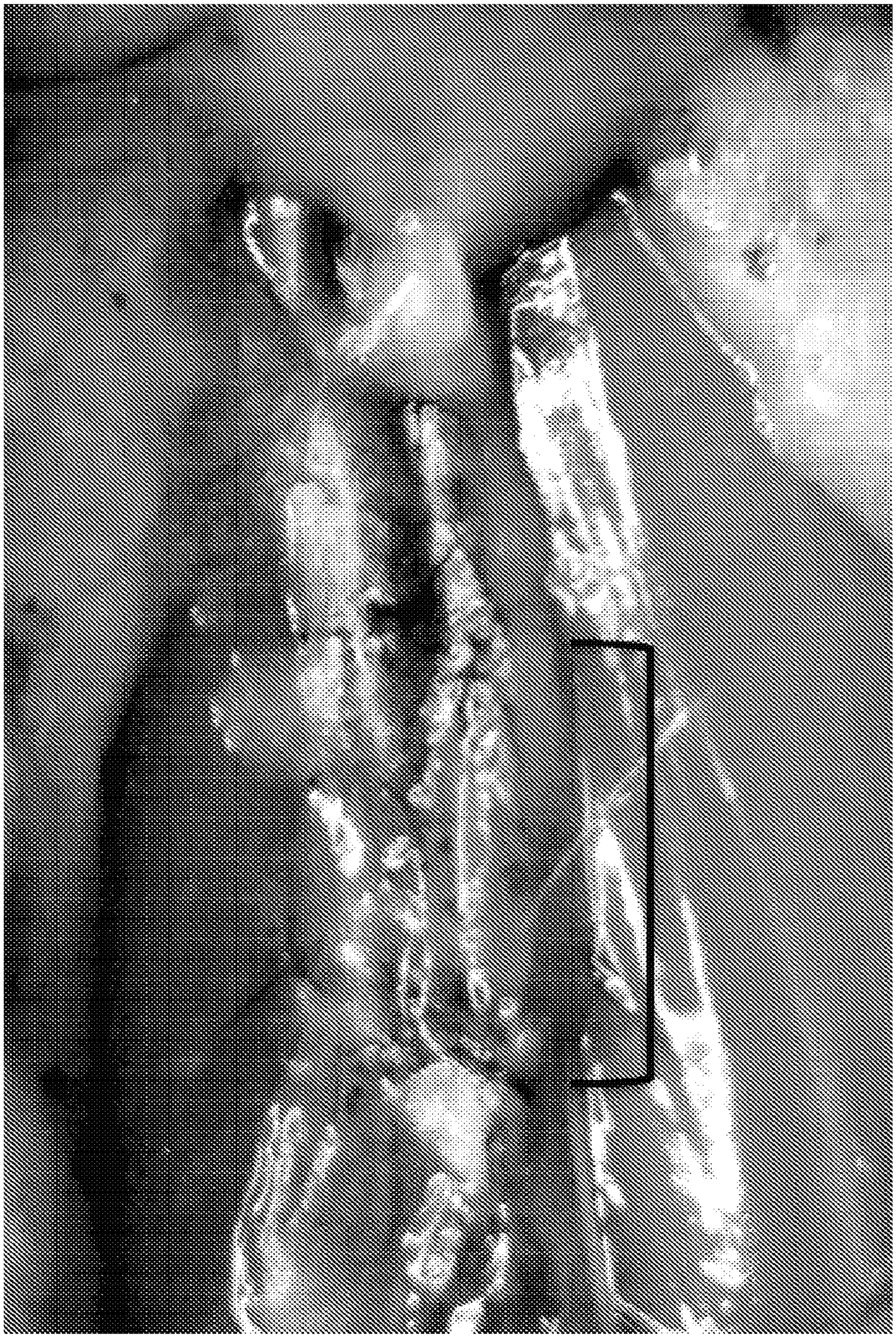
FIG. 12 is an image depicting a rat aortic interposition model (explant at 4 weeks). Implants are monitored by ultrasound.
Figure 13:
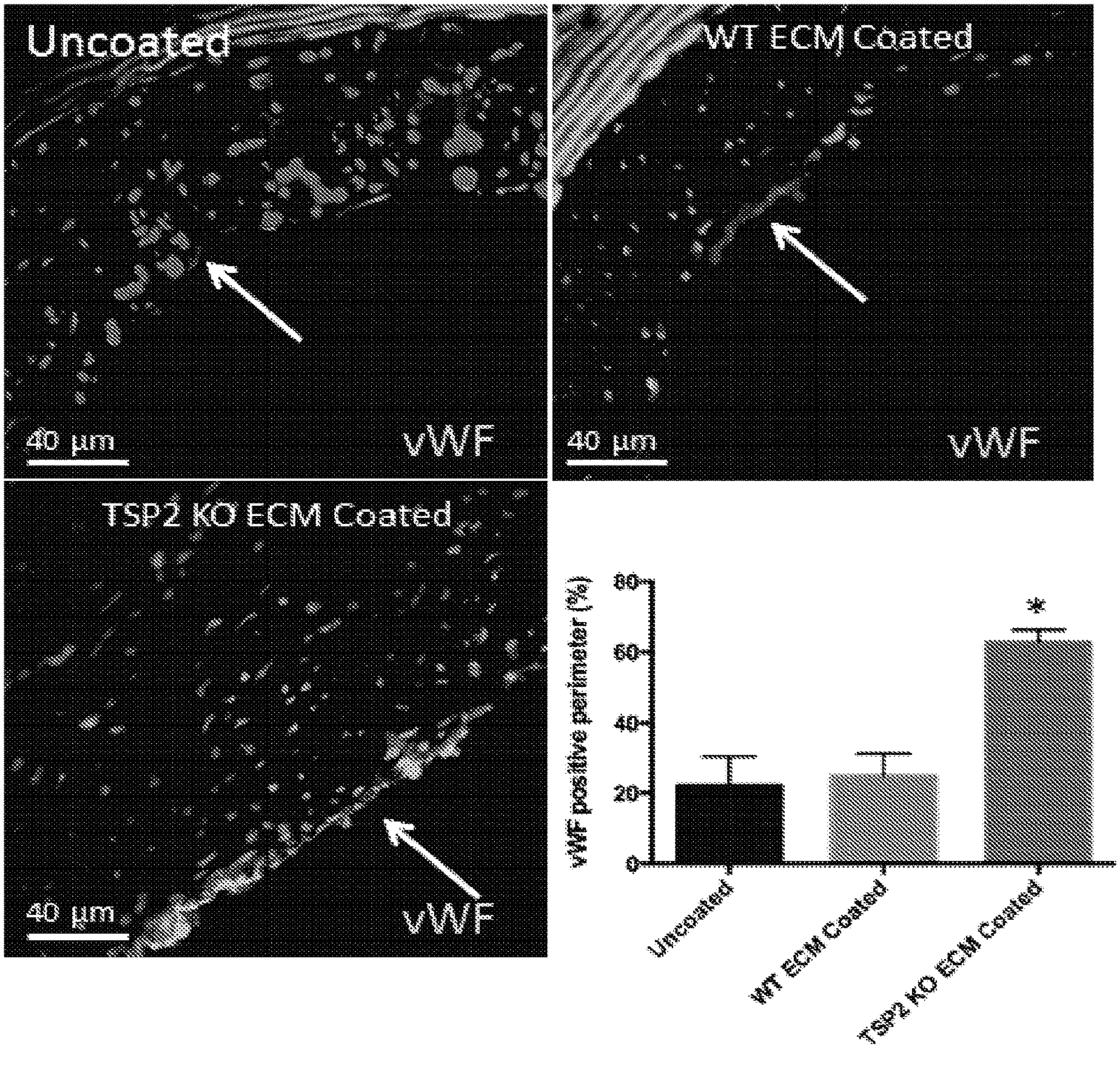
FIG. 13 a series of images and histograms demonstrating that there is significantly more endothelial coverage in TSP2 KO ECM modified/coated grafts. vWF was stained to allow visualizing the endothelium (Arrow indicated lumen surface).

Example 4: WT and TSP2 KO ECM is Expressed and Deposited in Similar Quantities and Patterns, and ECM and Modified Graft Mechanical Properties are Unchanged Next the ECM expression and deposition by TSP2 KO and WT dermal fibroblasts were examined. It was previously reported that collagen fibrils in TSP2 KO ECM are irregular in shape as compared to collagen fibrils in WT ECM in vitro (Krady et al., Am J Pathol. 2008; 173(3):879-891; Morris & Kyriakides, Matrix Biol. 2014; 37:183-191). In an attempt to identify differences in individual components of WT and KO ECM, immunofluorescence was performed for collagens I, IV, and VI, and fibronectin (FIG. 4A), as well as for collagen III, laminin and decorin (FIG. 8). Immunofluorescence showed similar deposition patterns in WT and TSP2 KO ECM for all components analyzed. Moreover, SEM imaging of WT and TSP2 KO ECM did not reveal striking differences, except that WT collagen fibrils were more aligned than those of TSP2 KO matrix (FIGS. 4B-4C, respectively). RT-PCR showed that there was no difference in mRNA content for collagens I, III, IV, V, VI, fibronectin, or decorin between WT and TSP2 KO cells (FIG. 4D).

Figure 4E:
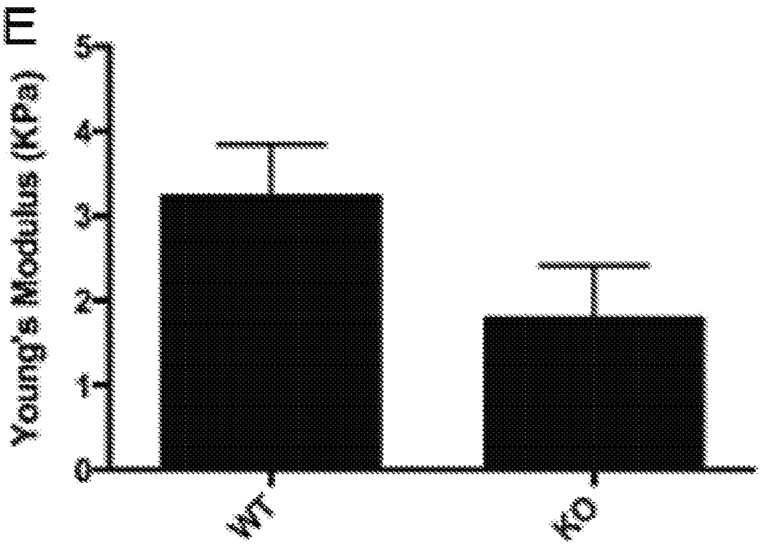
Figure 4F:
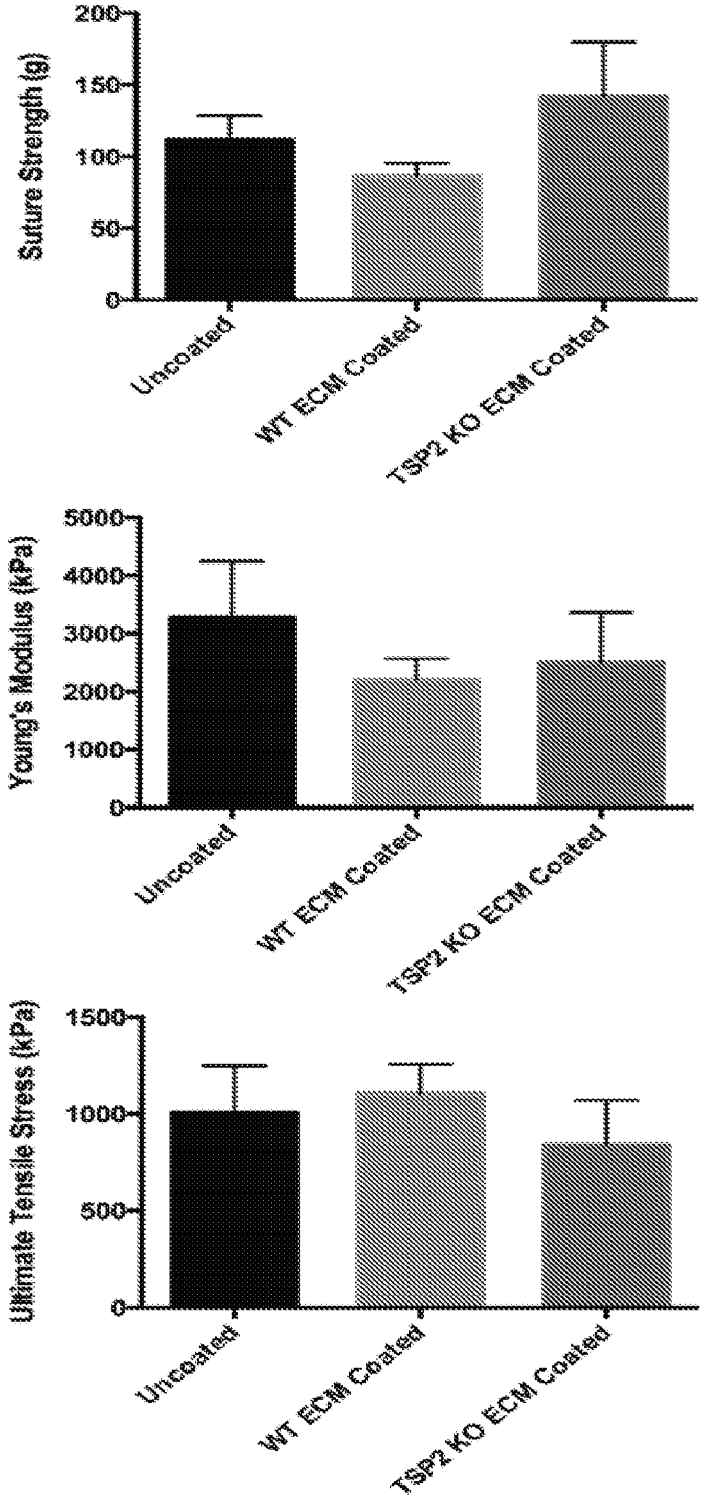

It is known that skin from TSP2 KO mice is less stiff than comparable tissue from WT animals, as measured by tensile testing (Kyriakides et al., The Journal of Cell Biology. 1998; 140(2):419-430). However, until recently it has been difficult to confirm whether this property is retained in cell-derived matrix. AFM is a method for measuring the mechanical properties of thin and delicate materials, such as hydrogels and cell-derived ECM (Soucy et al., Acta Biomater. 2011; 7(1):96-105). Therefore, the stiffness of WT and TSP2 KO ECM was determined using this method, and while a trend toward decreased stiffness of TSP2 KO ECM was found as compared to WT ECM, the difference was not significant (n=8) (FIG. 4E). To demonstrate further that the graft modification process does not alter mechanical properties of grafts, decellularized, unmodified and ECM modified (10 days) grafts were subjected to suture strength and INSTRON uniaxial testing (FIG. 4F). There were no differences found among the groups for suture strength (n=3), Young's modulus or ultimate tensile strength (n=6), indicating that the modification process does not affect the mechanical properties of the grafts.

Figures 5A, 5B, 5C, 5D, 5E:
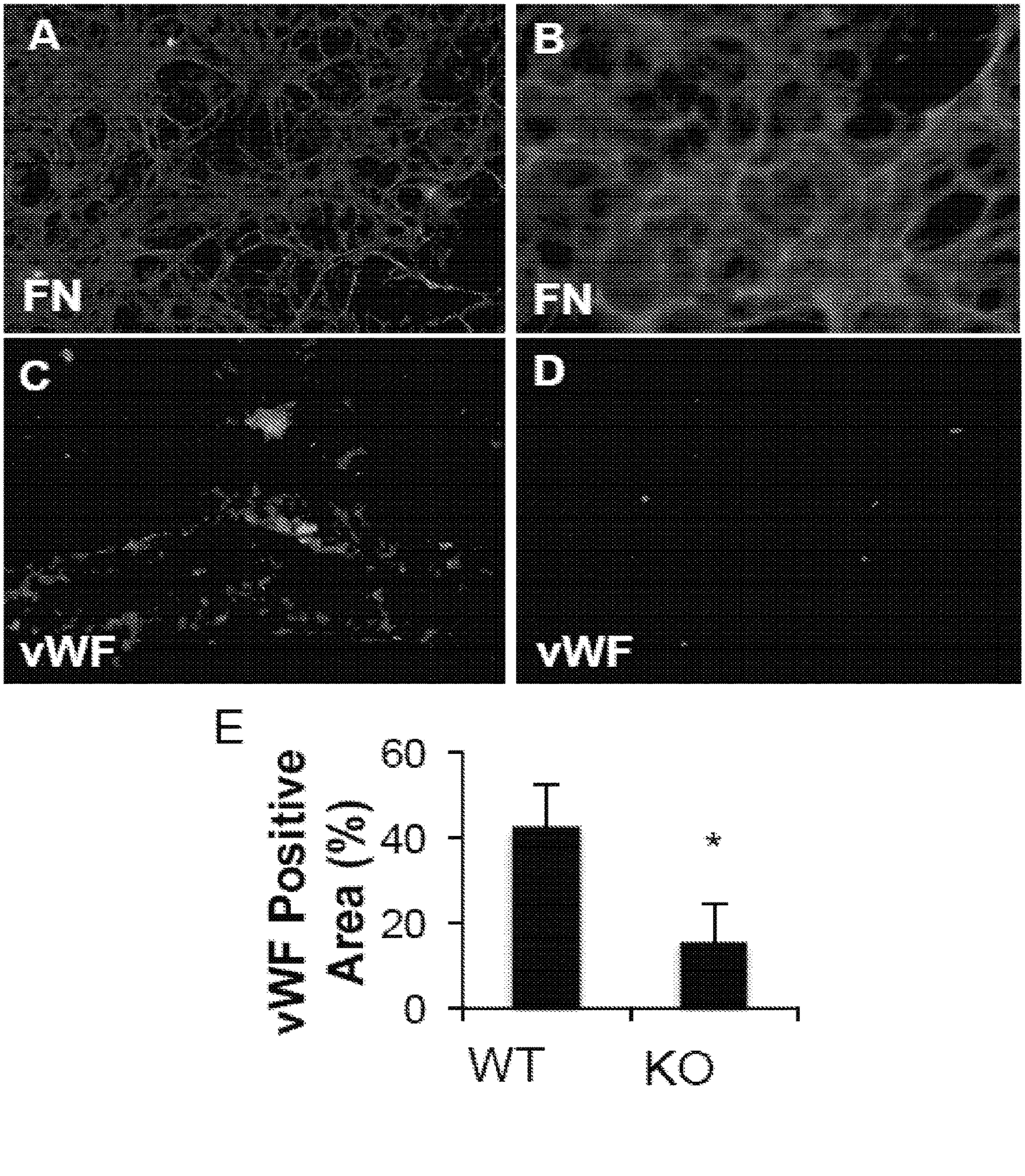
FIGS. 5A-5E, are a series of images and histograms demonstrating that reduced interaction of vWF with TSP2 KO derived ECM. Dermal fibroblasts from WT (FIG. 5A, FIG. 5C) and TSP2 KO mice (FIG. 5B, FIG. 5D) mice were cultured for 10 days and then removed by decellularization. ECMs were then exposed to plasma under flow (15 dynes/cm$^2$) for 15 min.

Example 5: Von Willebrand Factor (vWF) Binding to TSP2 KO Matrix is Deficient vWF plays a critical role in thrombus formation, as it is capable of binding to both exposed collagen and platelets. The binding of vWF to WT and TSP2 KO ECM was examined, using a system in which either WT or TSP2 KO ECM was deposited on glass slides. These slides were then placed in a flow chamber and human plasma was passed over the ECM at physiological flow rates (15 dynes/$cm^2$). After having been exposed to plasma under flow for up to 15 minutes, WT and TSP2 KO ECM was examined via immunofluorescence for fibronectin, to ensure ECM had not been dislodged by flow (FIGS. 5A and 5B) as well as for vWF (FIGS. 5C and 5D). Immunofluorescence detection of vWF showed a decrease in the amount of plasma-derived vWF binding to TSP2 KO ECM as compared to WT ECM (FIG. 5E).

Example 6: AFM Analysis Shows Distinct vWF Adhesion Forces

Figures 6A, 6B:
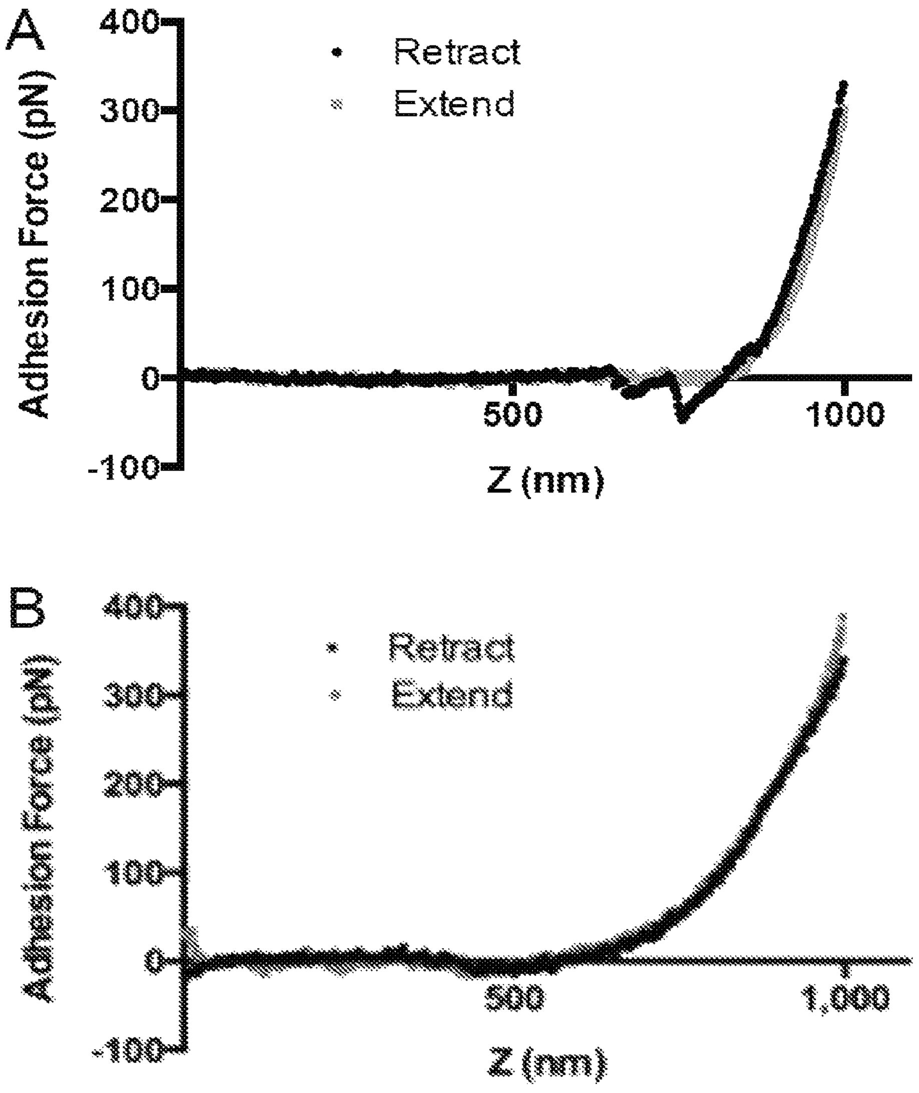
FIGS. 6A-6C are a series of graphs and histograms demonstrating that reduced vWF adhesion force on TSP2 KO derived ECM as measured by AFM. A vWF-conjugated 2 μm bead affixed to the end of an AFM cantilever was used to perform adhesion force studies. These studies were performed on decellularized day 7 ECM from WT and TSP2 KO dermal fibroblasts after BSA treatment, as well as on untreated and BSA-treated tissue culture plastic controls.
Figures 6C, 6D:
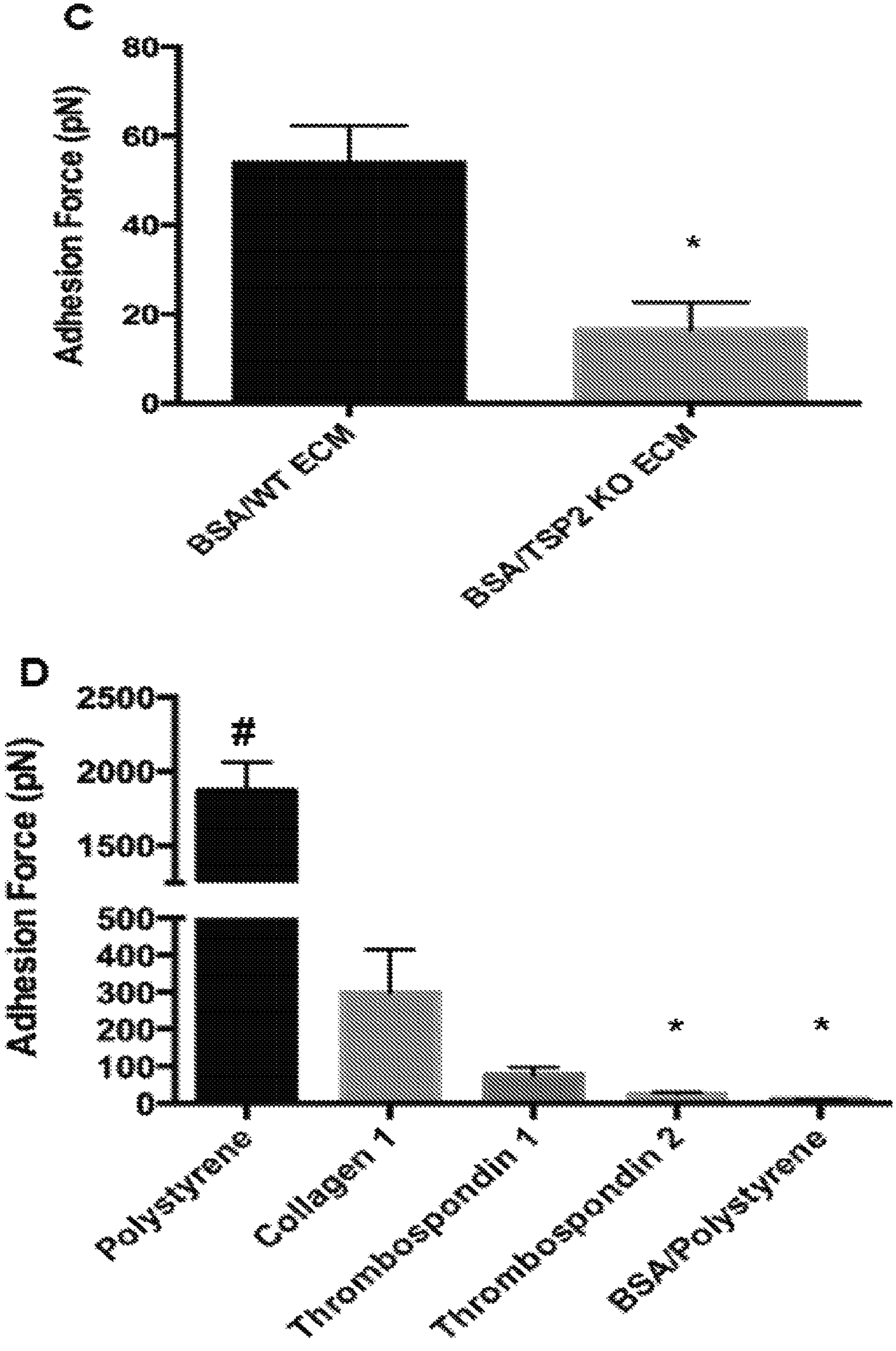

As mentioned above, TSP2 KO ECM showed a trend towards reduced stiffness in comparison to WT. However, the difference was not significant suggesting that it could not be the sole contributor for the lack of platelet response. To explore this defect further, an AFM approach was utilized that is capable of determining precise adhesion force measurements via a configuration involving a bead coated with adhesive proteins. This AFM technique has been used to measure adhesive forces involved in platelet adhesion, such as glycoprotein Ib-vWF adhesion as well as the adhesion forces involved in platelet integrin $\alpha_4\beta_1$-collagen peptide binding (Attwood et al., Int J Mol Sci. 2013; 14(2):2832-2845). Based upon the significant decrease in vWF staining in TSP2 KO ECM in vitro and in vivo, the adhesion force of vWF binding to cell-derived ECM was investigated. AFM studies in which vWF was conjugated to beaded cantilevers showed that there was adhesion of vWF to WT ECM. This was measured by calculating the difference in force between the nadir of the adhesion spike, which is characterized by the depression into negative values of force, in the retract curve and the corresponding values of the approach curve (FIG. 6A). Strikingly, no adhesion spike was seen in force curves from TSP2 KO ECM samples (FIG. 6B). Adhesion forces were quantified and vWF adhesion was decreased on TSP2 KO ECM (16.47±13 pN) compared to WT ECM (53.84±18 pN) (FIG. 6C). In addition, examination of vWF adhesion to purified proteins indicated adhesion to collagen I and TSP1 (positive controls), but not TSP2 (FIG. 6D).

Example 7: Rat TSP2 KO ECM Aortic Grafts have Less Occlusion

Similar to the above results, TSP2 KO ECM modified grafts were shown to be less susceptible to occlusion in a rat model as illustrated in FIGS. 9-13, FIGS. 17A-17I and FIGS. 18A-18B.

Unmodified decellularized aortic grafts or TSP2 KO ECM-modified decellularized aortic grafts were implanted in an infrarenal aortic interposition rat model. Results showed that unlike the uncoated grafts, none of the TSP2 KO ECM-modified grafts became critically stenotic (<75% occluded). In addition, TSP2 KO ECM-modified grafts showed an increase in cell ingrowth into the media which is beneficial toward producing grafts resembling native tissues. At 4 weeks in vivo, TSP2 KO ECM modified grafts were shown to have an improved patency rate and a decreased rate of critical stenosis (FIGS. 17A-17I). Furthermore, a better host/recipient endothelial cells coverage was achieved on the implanted TSP2 ECM modified grafts as compared to unmodified grafts.

Figures 16A, 16B, 16C, 16D, 16E, 16F:
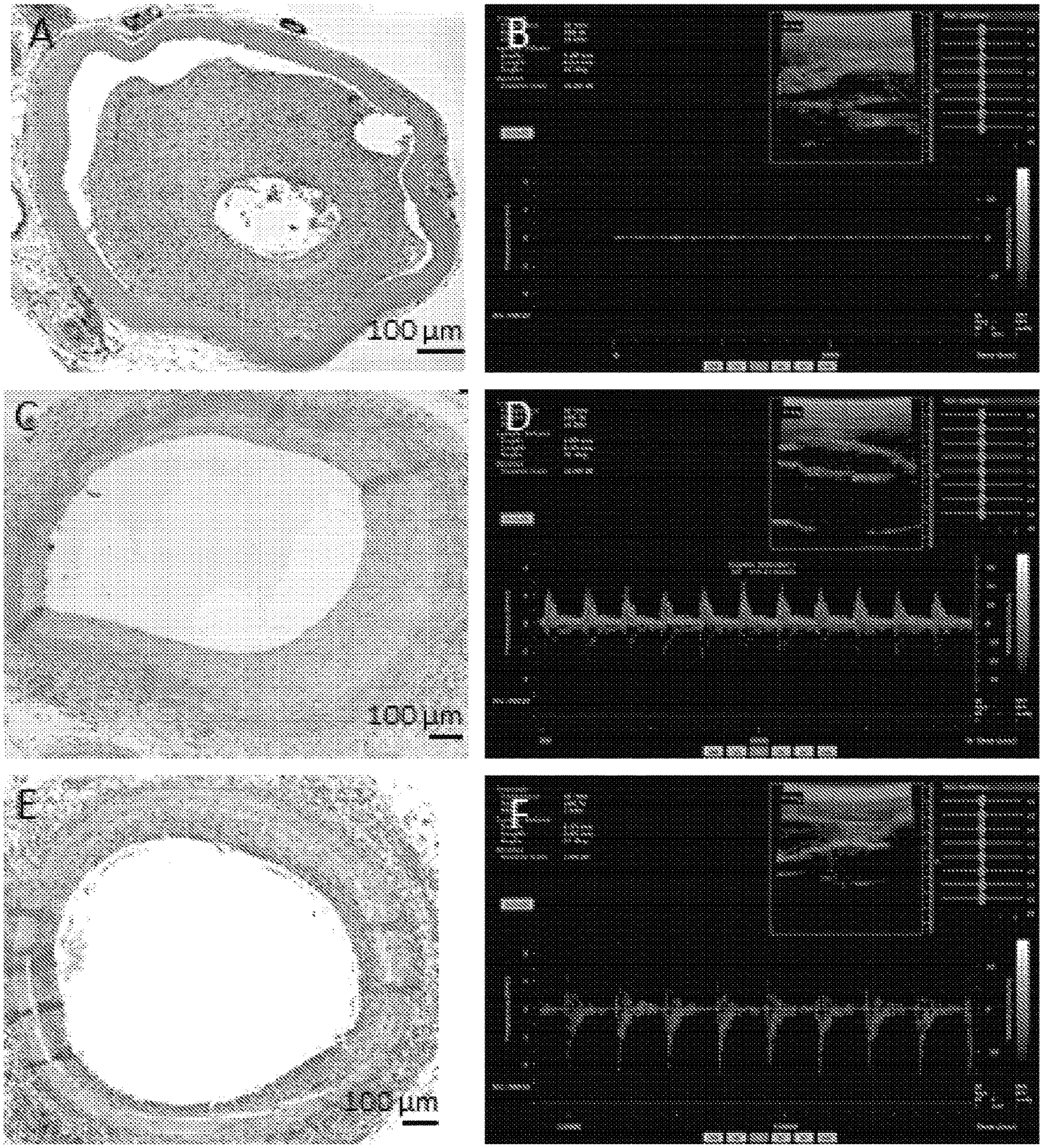
FIGS. 16A-16F are a series of images depicting graft patency's monitoring via ultrasound. After implantation, grafts were monitored weekly for flow. In critically stenosed grafts, such as the uncoated graft in (FIG. 16A), a significantly reduced flow was found at two weeks (FIG. 16B). In patent grafts, such as the WT ECM coated (FIG. 16C) and TSP2 KO ECM coated grafts (FIG. 16E), a blood flow was found through the graft at two weeks (FIG. 16D and FIG. 16F, respectively).
Figures 17A, 17B, 17C, 17D, 17E, 17F:
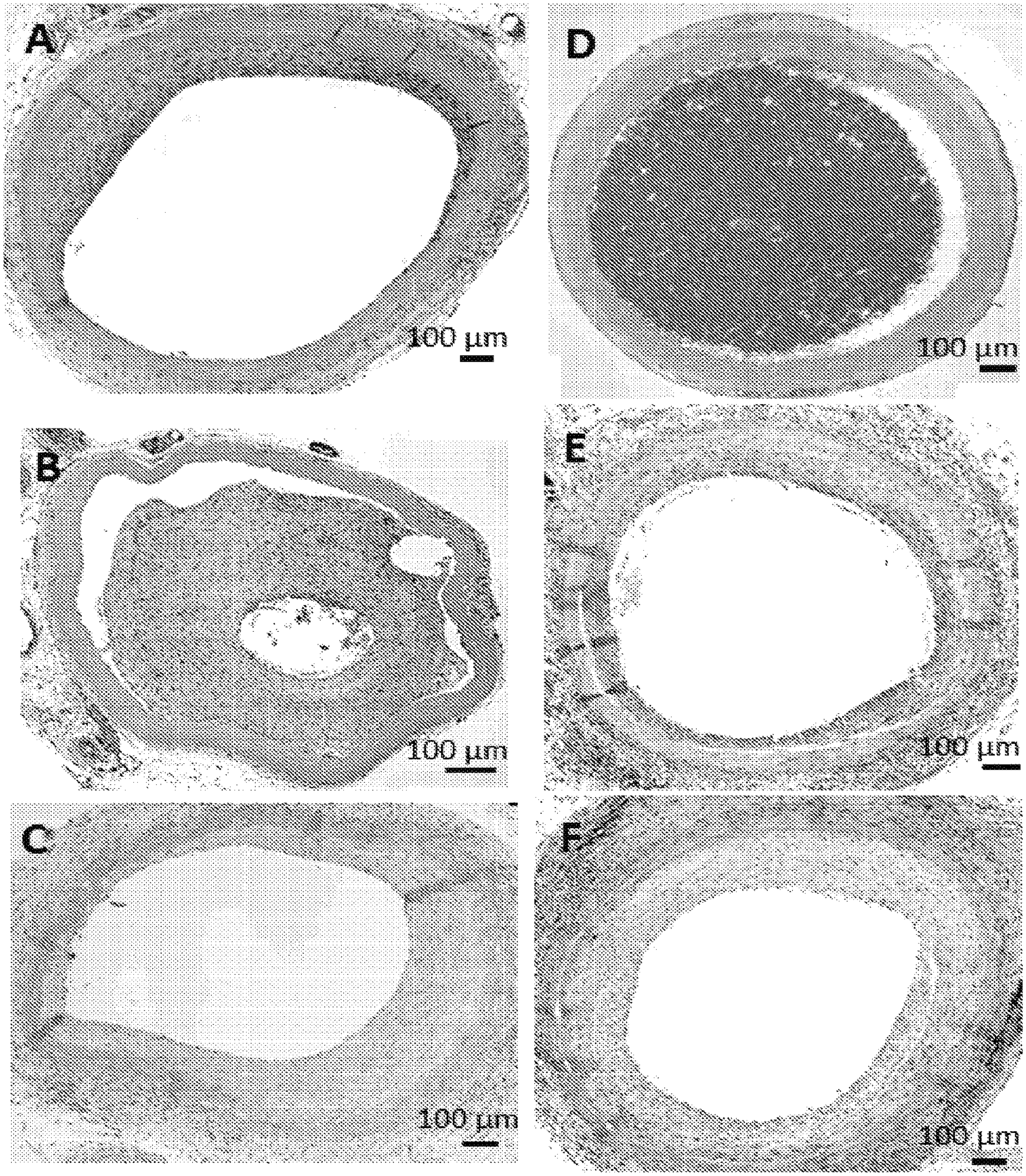
FIGS. 17A-17I are a series of images and histograms demonstrating that TSP2 KO ECM coated grafts have an improved patency rate at 4 weeks in vivo. A range of representative H&E images of uncoated (FIGS. 17A-17B) WT ECM coated (FIGS. 17C-17D) and TSP2 KO ECM (FIGS. 17E-17F) coated grafts after 4 weeks implanted in rat aortas. Quantification of the outer diameters of the grafts using Image J revealed no significant differences among groups (FIG. 17G). Quantification of the percentage of the area occluded by tissue ingrowth using Image J showed a trend toward decreased percent occlusion in TSP2 KO ECM coated grafts (FIG. 17H). In addition, TSP2 KO ECM coated grafts showed a decreased rate of failure (I). n=9, $*p<0.05$.
Figures 17G, 17H, 17I:
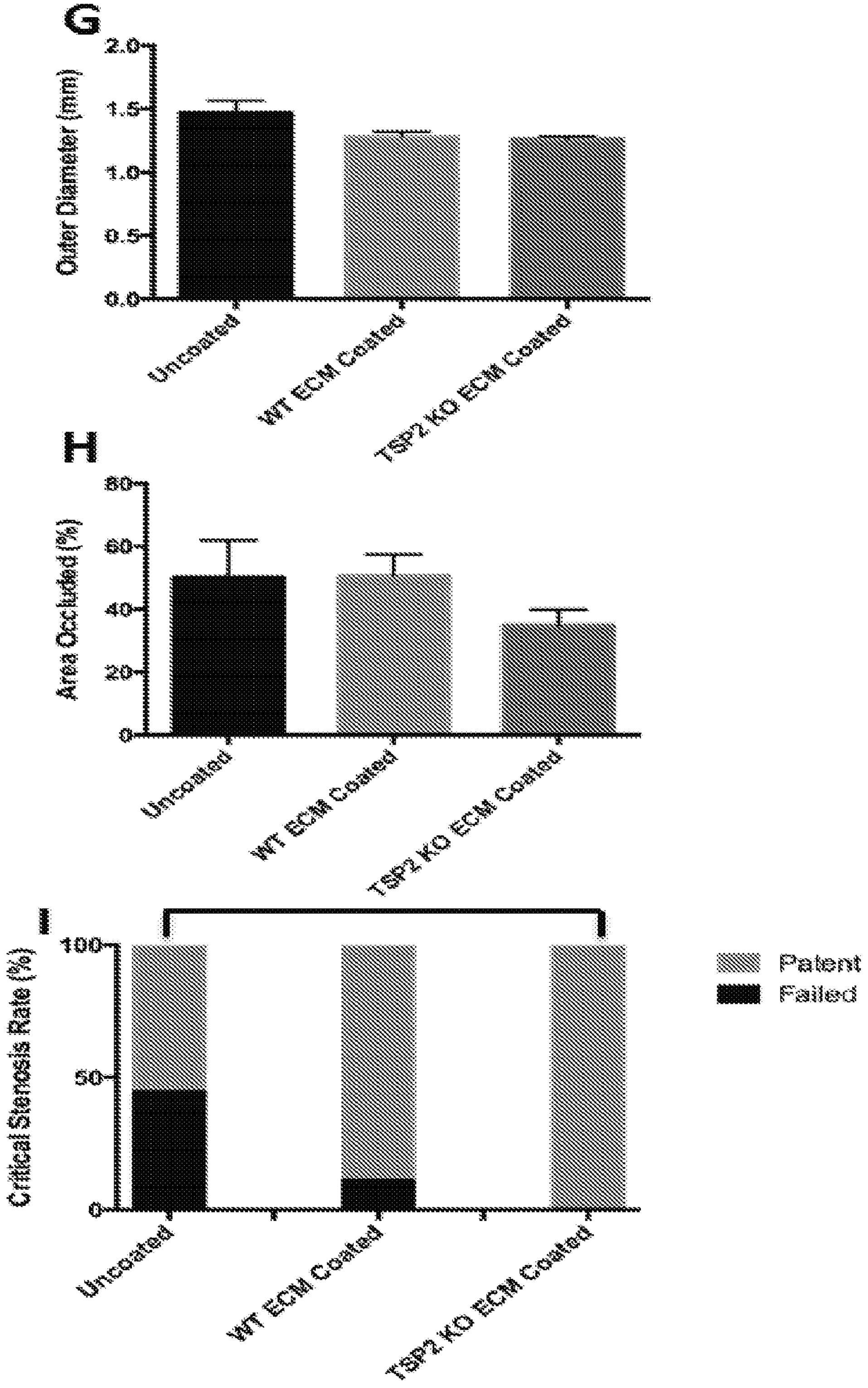
Figure 18A:
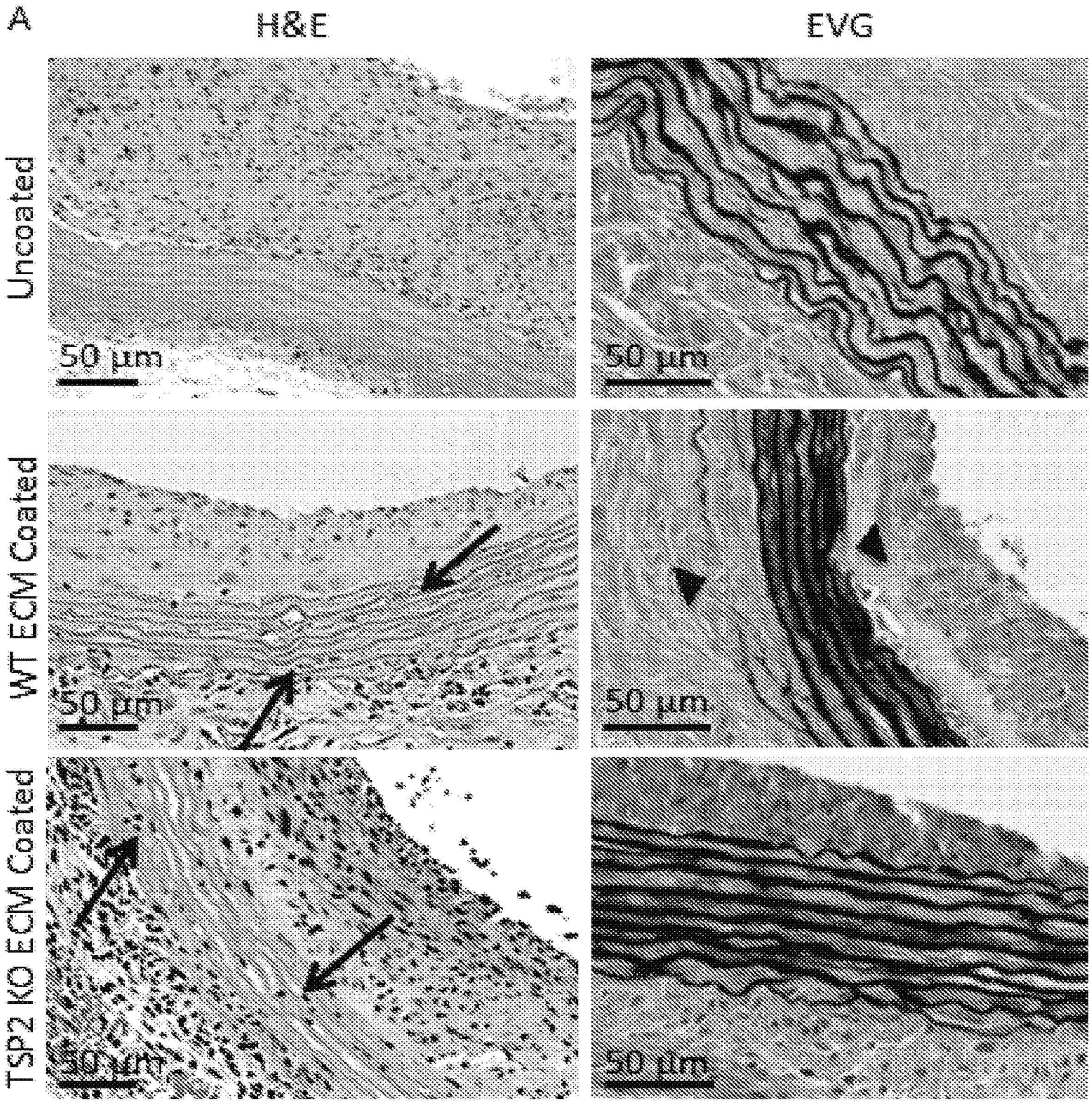
FIGS. 18A-18B are a series of images and histograms showing that cell ingrowth into the media of the graft is significantly higher in TSP2 KO ECM coated grafts. Also WT ECM coated grafts were found to have incomplete elastic laminae (indicated by arrowhead). n=6, $p<0.05$.
Figure 18B:
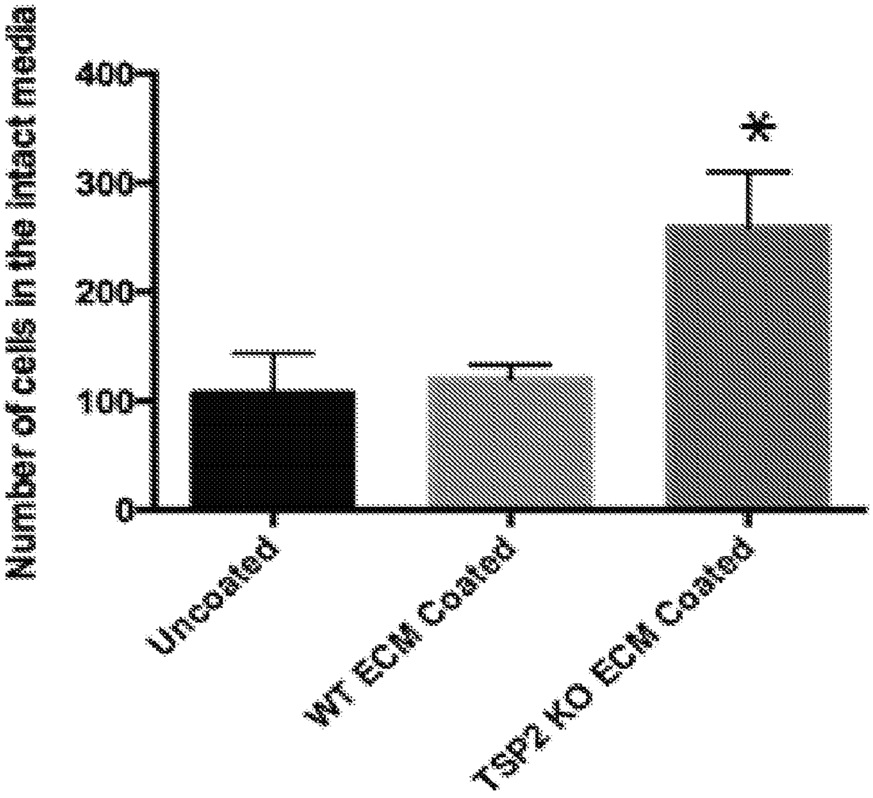

Additionally, graft patency was monitored via ultrasound. After implantation, grafts were monitored weekly for blood flow (FIGS. 16A-16F). In critically stenosed grafts, such as the unmodified, uncoated graft in (FIG. 16A), a significant reduction of blood flow was found at two weeks (FIG. 16B). In patent grafts, such as the WT ECM modified (FIG. 16C) and TSP2 KO ECM modified grafts (FIG. 16E), the blood flow was consistently present through the graft at two weeks (FIG. 16D and FIG. 16F, respectively).

Figure 14:
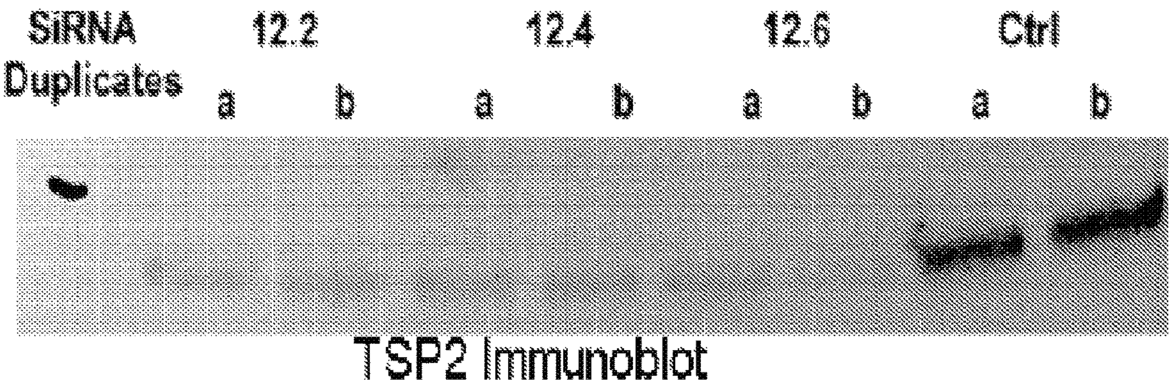
FIG. 14 is an image demonstrating successful TSP2 knock down in canine SMCs.TSP2 KD was produced in canine smooth muscle cells using small interferening (siRNA) and knock down was determined to be achieved as shown in a western blot using multiple TSP2 siRNA sequences (labeled 12.2, 12.4, 12.6). It is clear that TSP2 expression was much lower in cells treated with siRNA as compared to untreated controls.
Figure 15:
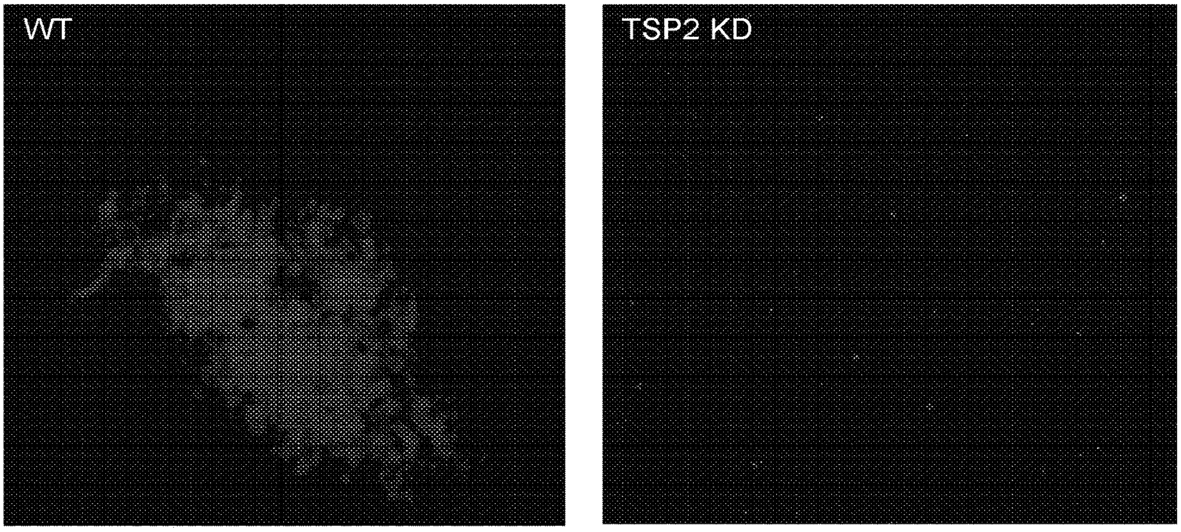
FIG. 15 is a series of images demonstrating that TSP2 KD is sufficient to prevent platelet adhesion to ECM. Immunofluorescence images showing platelet response to wild-type canine smooth muscle (WT, SMC) ECM and to TSP2 KD SMC ECM. A decrease in platelet adhesion was clearly seen in the TSP2 KD ECM. Platelet were stained red using rhodamine-phalloidin.

Example 8: ECM with TSP2 Knock Down (KD) is Sufficient to Prevent Platelet Adhesion To validate this invention in other higher order mammals, TSP2 knock down (TSP2 KD) was produced in canine smooth muscle cells using small interfering (siRNA). ECM with TSP2 KD was determined to be sufficient to deter platelet adhesion. Experiment results showed that TSP2 expression was much lower in cells treated with siRNA as compared to untreated controls (FIG. 14) and that platelet adhesion was clearly reduced in ECM with TSP2 KD cells as compared to wild-type ECM cells (FIG. 15).

Example 9: Successful TSP2 KO ECM Modification in Pig Aortic Grafts

Figures 19A, 19B, 19C, 19D:
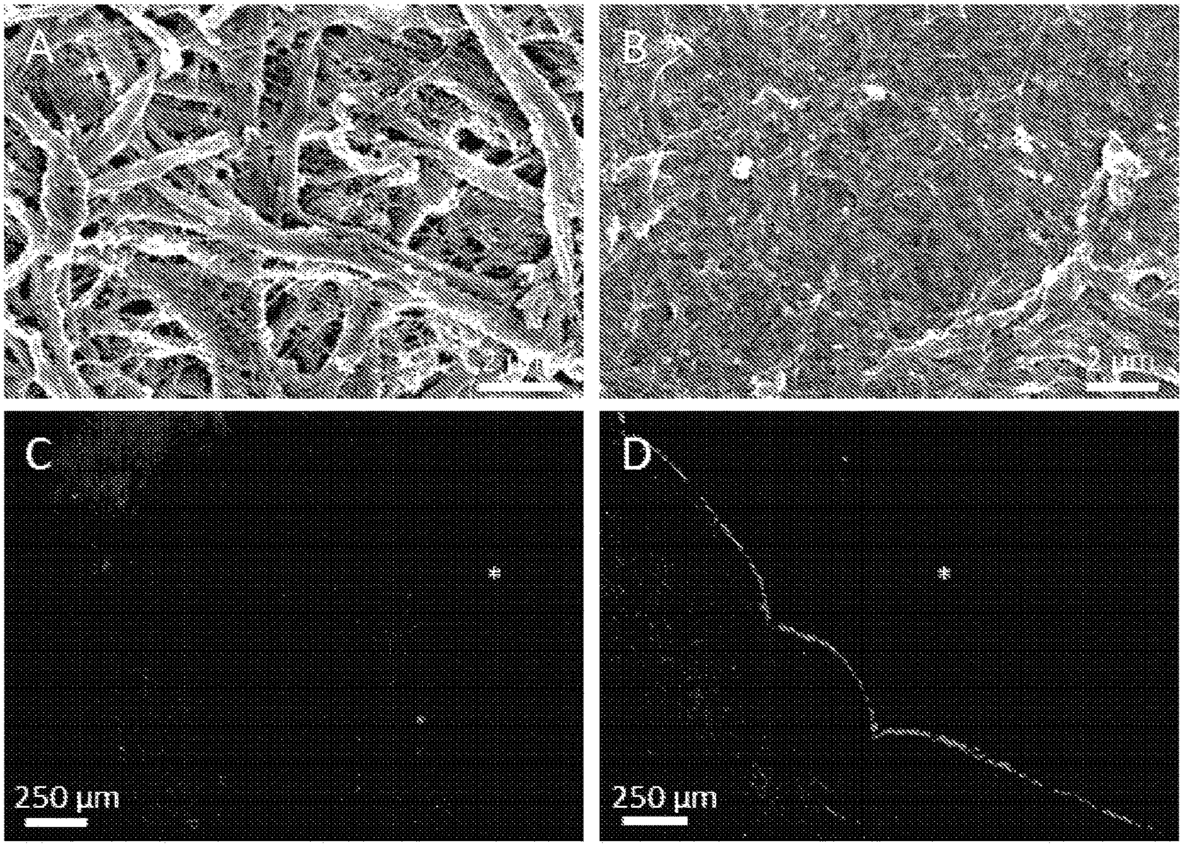
FIGS. 19A-19D are a series of images demonstrating that TSP2 KO ECM can be successfully deposited in grafts of various animal models such as the lumen of decellularized pig aortas. Pig aortas were decellularized (FIG. 19A and FIG. 19C). The lumens were seeded with TSP2 KO fibroblasts and cultured for 7 days before a second decellularization. Images of these grafts (FIG. 19B and FIG. 19D) clearly indicate a TSP2 KO ECM coating has been deposited.
Figures 20A, 20B, 20C, 20D, 20E:
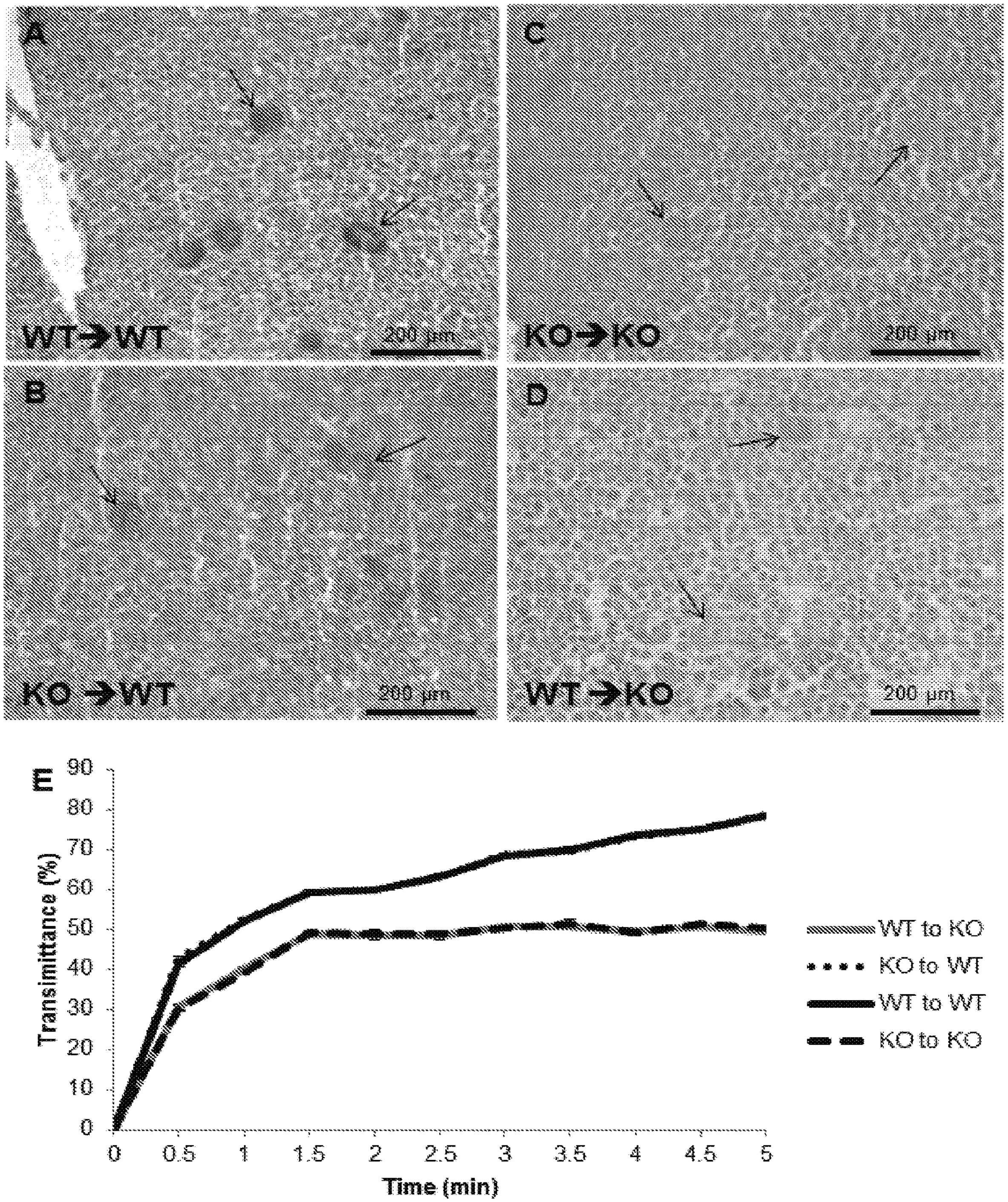
FIGS. 20A-20E are a series of images and a graph illustrating bone marrow transplant histology and platelet aggregation.

As shown in FIGS. 19A-19D, TSP2 KO ECM can be successfully deposited in grafts of various animal models such as the lumen of decellularized pig aortas. Pig aortas were decellularized (FIG. 19A and FIG. 19C). The lumens were seeded with TSP2 KO fibroblasts and cultured for 7 days before a second decellularization. Images of these grafts (FIG. 19B and FIG. 19D) clearly indicate a TSP2 KO ECM modification occurred and coating has been deposited. It is known in the art that decellularized ECM graft products from higher order mammal sources (e.g. porcine or bovine) are currently used in humans heart valves, pericardial patches or skin grafts to name a few. Therefore, similar higher order mammal are suitable for making grafts products with ECM TSP2 knock down that would be valuable for human use.

Example 10: Overview

The formation of ECM in association with cells is a complex process that is not well understood. In order to gain a better understanding of the role of molecules modulating the nucleation and cellular assembly of ECM, many researchers have endeavored to knock down their expression. Studies focused on collagen V, a molecule thought to be important in nucleation of collagen I fibrils and the molecule associated with Ehlers-Danlos syndrome, have shown that genetic ablation of the al component of collagen V leads to mechanical failure of skin at lower stresses. They have also shown that deletion of either the α1 or α2 components of collagen V results in larger, more irregularly shaped collagen fibrils. Similar studies focused on lumican and decorin, which have been shown to increase interfibrillar spacing in acellular models, also yielded more delicate skin and connective tissue, as well as larger and irregular collagen fibrils compared with WT controls. In fact, it has been proposed that decorin-associated glycosaminoglycans act not only in fibril assembly, but also as bridges capable of transferring forces between fibrils. So, it is possible that these kinds of molecules are not only important in the assembly of regular fibrils, but may also add to the mechanical integrity of the mature fibers in connective tissues.

Large, abnormal collagen fibers and decreased mechanical strength of skin are also prominent aspects of the TSP2 KO mouse phenotype. However, repeated attempts to localize TSP2 in collagen fibers were unsuccessful. The inability noted herein to demonstrate TSP2 as an integral component of the collagen fibril suggested that the abnormality in the TSP2 KO mice could be due to a defect in collagen assembly by fibroblasts.

The interaction of platelets with TSP2 KO ECM was examined in the present invention. However, as reported herein, ECM assembled by fibroblasts that lack TSP2 does not support platelet aggregation. The fact that exposure of platelets to TSP2 KO ECM does not result in platelet aggregation is abnormal. In healthy vessels, the ECM serves as a scaffold for the ECs, smooth muscle cells (SMCs), and fibroblasts that populate the tissue, with the ECs forming a barrier between the ECM and the blood. When the vessel is damaged, however, interactions between collagenous ECM and vWF have been shown to be critical for hemostasis and thrombosis. Once vWF is bound to collagen, it may in turn be bound by the platelet glycoprotein Ibα. This tethers the platelet to the disruption in the endothelium, and is the first step towards thrombosis (Szanto et al., Semin Thromb Hemost. 2012; 38(1):55-63). Simply by being accessible, the ECM sets a crucial chain of events in motion. The fact that TSP2 KO matrix does not seem to initiate this cascade is unusual. In order to elucidate a mechanism for this finding, the expression and deposition patterns of components of WT and TSP2 KO ECM were examined herein. In addition, AFM, an advanced but increasingly popular technique for the measurement of mechanical properties of delicate materials, was utilized to examine the stiffness of and ability of fibroblast-derived TSP2 KO ECM to support vWF adhesion. Notably, this information could offer a potential mechanistic explanation for the reported platelet adhesion defect, as recent studies have shown that fibrin and collagen immobilized on stiffer substrates are more likely to activate platelets (Qiu et al., Proc Natl Acad Sci USA. 2014; 111(40):14430-14435; Kee et al., PLoS One. 2015; 10(4): e0126624). Analysis of adhesion strength of a 2 μm bead coated with vWF showed decreased adhesion force to TSP2 KO ECM, which was consistent with plasma flow studies showing reduced vWF accumulation on TSP2 KO ECM. It should be noted that the inherent stiffness of TSP2 KO ECM was somewhat reduced and could also contribute to compromised platelet responses. Collagen fibril assembly by TSP2 KO dermal fibroblasts was previously shown to be irregular, and cryptic collagen epitopes to be exposed in TSP2 KO ECM (Krady et al., Am J Pathol. 2008; 173(3): 879-891). As such, the failure of vWF to bind due to the effect of TSP2 deficiency on the formation collagen fibrils is presently explored. This fibril irregularity in turn could obscure vWF binding sites, thus preventing the first step in the adhesion of platelets to the matrix.

The disclosures of each and every patent, patent application, and publication cited herein are hereby incorporated herein by reference in their entirety.

While the present invention has been disclosed with reference to specific embodiments, it is apparent that other embodiments and variations of the present invention may be devised by others skilled in the art without departing from the true spirit and scope of the invention. The appended claims are intended to be construed to include all such embodiments and equivalent variations.

What is claimed is:

1. A non-thrombogenic decellularized vascular graft comprising a lumen and an exogenous cell-derived extracellular matrix lacking thrombospondin-2 (TSP2-null ECM), wherein the cell-derived TSP2-null ECM is decellularized, wherein the cell-derived TSP2-null ECM is deposited onto the lumen by TSP-null ECM producing cells in contact with the lumen, wherein the graft is less adhesive for von Willebrand Factor (vWF) as compared to a reference graft comprising a lumen, wherein the reference graft is modified with a decellularized ECM not lacking TSP-2, and wherein a risk of developing a thrombosis in a recipient of the graft is reduced when the graft is transplanted into the recipient.

2. The non-thrombogenic decellularized vascular graft of claim 1, wherein, when the graft is transplanted into the recipient, the graft is reendothelialized by the recipient's endothelial cells.

3. The non-thrombogenic decellularized vascular graft of claim 1, wherein the graft is 10 millimeters or less in diameter.

4. The non-thrombogenic decellularized vascular graft of claim 1, wherein the graft is an aortic graft.

5. The non-thrombogenic decellularized vascular graft of claim 1, wherein the graft comprises a decellularized pig aorta.

6. The non-thrombogenic decellularized vascular graft of claim 1, wherein following transplantation of the graft in the recipient, blood flow is present through the graft two weeks after transplantation.

7. The non-thrombogenic decellularized vascular graft of claim 1, wherein the TSP-null ECM producing cells are in contact with the lumen for about 7 days.

8. A method for transplanting a non-thrombogenic decellularized vascular graft comprising a lumen to a subject in need thereof, the method comprising administering to the subject the non-thrombogenic decellularized vascular graft of claim 1 pretreated with a therapeutic agent in a pharmaceutically acceptable carrier.

* * * * *

SEQUENCE LISTING

```
<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1

tgactggaag agcggagagt act                                          23


<210> SEQ ID NO 2
<211> LENGTH: 19
<212> TYPE: DNA
<213> ORGANISM: Artificial Sequence
```

<220> FEATURE:
<223> OTHER INFORMATION: Primer

<400> SEQUENCE: 2
ccttgatggc gtccaggtt 19

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
ctgtaacatg gaaactgggg aaa 23

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
ccatagctga actgaaaacc acc 23

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
aacaacgtct gcaacttcgc 20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cttcacaaac cgcacacctg 20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cttcgccgct actcctgttc 20

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ccctgagggc aaattgtgaa aa 22

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
ctgctgctac aagcctgct 19

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
ccccataagg tttcagcctc a 21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gagaggagca ctaccccaga 20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gcccggatta aggttggtga 20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
aatgtgggtg tcagctggat 20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ctagcaaggt tgtgtcgggt 20